United States Patent
Phillips et al.

(10) Patent No.: US 7,200,531 B2
(45) Date of Patent: Apr. 3, 2007

(54) CONFORMATION-ACTIVITY RELATIONSHIP OF APOPTOSIS-INDUCING PHOSPHODIESTER OLIGONUCLEOTIDES

(75) Inventors: Nigel C. Phillips, Pointe-Claire (CA); Mario C. Filion, Laval (CA); Zdenek Richard Holan, Montreal (CA); Stéphanie Reader, Ste-Julie (CA)

(73) Assignee: Bionicrie Life Sciences, Inc., Belleville (CA)

( * ) Notice: Subject to any disclaimer, the term of this patent is extended or adjusted under 35 U.S.C. 154(b) by 226 days.

(21) Appl. No.: 10/223,234

(22) Filed: Aug. 19, 2002

(65) Prior Publication Data

US 2003/0144233 A1 Jul. 31, 2003

Related U.S. Application Data

(60) Provisional application No. 60/313,290, filed on Aug. 17, 2001.

(51) Int. Cl.
*G06G 7/58* (2006.01)
(52) U.S. Cl. .............................. 703/2; 703/11; 702/19
(58) Field of Classification Search .................. 702/27; 703/2, 11
See application file for complete search history.

(56) References Cited

U.S. PATENT DOCUMENTS 5,643,890 A    7/1997    Iversen et al.

FOREIGN PATENT DOCUMENTS

WO    WO 01/44465    6/2001

OTHER PUBLICATIONS

Bates, P., et al., Antiproliferative Activity of G-rich Oligonucleotides Correlates with Protein Binding, *J. Biol. Chem.*, vol. 274, No. 37, pp. 26369-26377 (1999).
Chen, H., et al., "Synthesis and Structure-activity Studies of a Series of [(Hydroxybenzyl)amino]Salicylates as Inhibitors of EGF Receptor-associated Tyrosine Kinase Activity", *J. Med. Chem.*, vol. 36, No. 25, pp. 4094-4098 (1993) (Abstract Only).
Dimri, G., et al., "A Biomarker that Identifies Senescent Human Cells in Culture and in Aging Skin *In Vivo*", *Proc. Natl. Acad. Sci USA*, vol. 92, pp. 9363-9367 (1995).
Evrard-Todeschi, N., et al., "Predictive Study by Molecular Modeling to Promote Specific Probes of Glutamate Receptors, Using Methylated Cyclic Glutamic Acid Derivatives (trans-and cis-ACPD). Comparison with Specific Agonists.", *J. Chem. Inf. Comput. Sci.*, vol. 38, No. 4, pp. 742-760 (1998) (Abstract Only).
Filion, M., et al., "Pro-apoptotic and Terminal Differentiation Activity of 6 Base Length Phosphodiester Oligonucleotide, Oligomodulator™ BT 99-25, Towards Leukemia Cells", Program and Abstracts of the 6th International Symposium held at L'Institut Pasteur, Paris, France, No. 155 (Oral Session 1092), p. S-93 (2002).

(Continued)

*Primary Examiner*—Marjorie A. Moran
(74) *Attorney, Agent, or Firm*—Kilpatrick Stockton LLP

(57) ABSTRACT

The present invention facilitates in silico evaluation of molecules for biological activity by providing a computer-based method to predict whether oligonucleotides may possess biological activity and the efficacy of the biological activity based on the three-dimensional structure and charge characteristics of the oligonucleotides. Biological activities include, but are not limited to, cellular proliferation, induction of cell cycle arrest and apoptosis.

16 Claims, 58 Drawing Sheets
(46 of 58 Drawing Sheet(s) Filed in Color)

OTHER PUBLICATIONS

Guarna, A., et al., "19-nor-10-azasteroids, a New Glass of Steroid 5 Alpha-reductase Inhibitors, 2. X-ray Structure, Molecular Modeling, Conformational Analysis of 19-nor-10-azasteroids and Comparison with 4-azasteroids and 6-azasteroids", *J. Med. Chem.*, vol. 40, No. 21, pp. 3466-3477 (1997) (Abstract Only).

Hochhauser, D., "Modulation of Chemosensitivity Through Altered Expresion of Cell Cycle Regulatory Genes in Cancer", *Anticancer Drugs*, vol. 8, No. 10, pp. 903-910 (1997) (Abstract Only).

Koopman, G. et al., "Annexin V for Flow Cytometric Detection of Phosphatidylserine Expression on B Cells Undergoing Apoptosis", *Blood*, vol. 84, No. 5, pp. 1415-1420 (1994) (Abstract Only).

Mata, J. et al., "A Hexameric Phosphorothioate Oligonucleotide Telomerase Inhibitor Arrests Growth of Burkitt's Lymphoma Cells *in Vitro* and *in Vivo*", *Toxicol. Appl. Pharmacol.*, vol. 144, pp. 189-197 (1997).

Morassutti, C. et al., "Effect of Oligomer Length and Base Substitutions on the Cytotoxic Activity and Specific Nuclear Protein Recognition of GTn Oligonucleotides in the Human Leukemic CCRF-CEM Cell Line", *Nucleosides & Nucleotides*, vol. 18, Nos. 6 & 7, pp. 1711-1716 (1999).

Read, M. et al., "Structure-based Design of Selective and Potent G Quadruplex-mediated Telomerase Inhibitors", *Proc. Natl. Acad. Sci. USA*, vol. 98, No. 9, pp. 4844-4849 (2001).

Scaggiante, B., et al., Human Cancer Cell Lines Growth Inhibition by $GT_n$ Oligodeoxyribonucleotides Recognizing Single-stranded DNA-binding Proteins, *Eur. J. Biochem.*, vol. 252, pp. 207-215 (1998).

Vlassov, V., et al., "Transport of Oligonucleotides Across Natural and Model Membranes", *Biochim. Biophys. Acta*, vol. 1197, No. 2, pp. 95-108 (1994).

Wagner, R., "Gene Inhibition Using Antisense Oligodeoxynucleotides", *Nature*, vol. 372, pp. 333-335 (1994).

Kandimalla, E. R., et al., "Effect of Chemical Modifications of Cytosine and Guanine in a CpG-Motif of Oligonucleotides: Structure-immunostimulatory Activity Relationships", Bioorganic & Medicinal Chemistry, vol. 9, pp. 807-813 (2001).

Reader, S., et al., "Identification of Non-Antisense Phosphodiester Oligonucleotides that Induce Cell Cycle Arrest and Apoptosis in Cancer Cells", Clinical Cancer Research, The American Association for Cancer Research, vol. 6, p. 526, (2000).

International Search Report issued in International Patent Application No. PCT/IB02/03324, mailed Apr. 16, 2004.

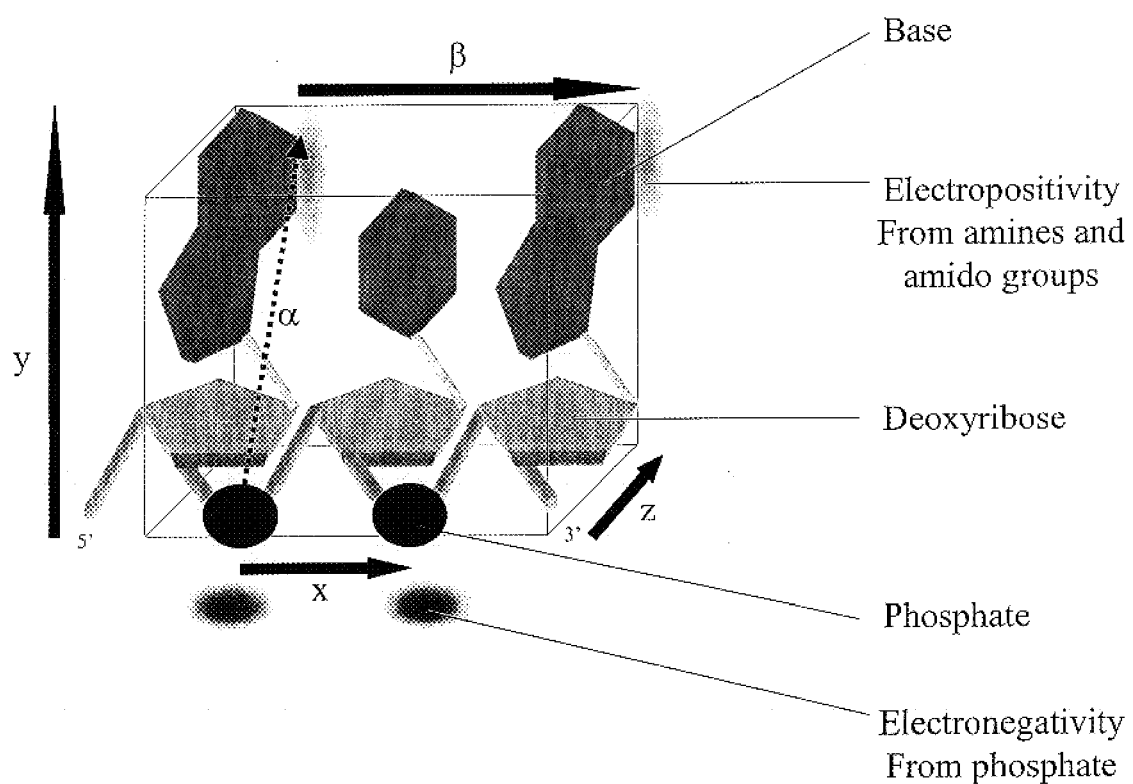

CONFORMATION-ACTIVITY RELATIONSHIP OF APOPTOSIS-INDUCING PHOSPHODIESTER OLIGONUCLEOTIDES

PRIOR RELATED APPLICATIONS

The present application claims benefit of priority to U.S. Provisional patent application Ser. No. 60/313,290 filed Aug. 17, 2001.

FIELD OF THE INVENTION

The present invention provides a computer-based method to predict whether oligonucleotides may induce apoptosis in cancer cells based on the three-dimensional structure and charge characteristics of the oligonucleotides.

BACKGROUND OF THE INVENTION

Cancer is an aberrant net accumulation of atypical cells, which can result from an excess of proliferation, an insufficiency of cell death, or a combination of the two.

Proliferation is the culmination of a cell's progression through the cell cycle resulting in the division of one cell into two cells. The five major phases of the cell cycle are $G_0$, $G_1$, S, $G_2$, and M. During the $G_0$, phase, cells are quiescent. Most cells in the body, at one time, are in this stage. During the $G_1$ phase, cells, responding to signals to divide, produce the RNA and the proteins necessary for DNA synthesis. During the S-phase (SE, early S-phase; SM, middle S-phase; and SL, late S-phase) the cells replicate their DNA. During the $G_2$ phase, proteins are elaborated in preparation for cell division. During the mitotic (M) phase, the cell divides into two daughter cells. Alterations in cell cycle progression occur in all cancers and may result from over-expression of genes, mutation of regulatory genes, or abrogation of DNA damage checkpoints (Hochhauser D., Anti-Cancer Chemotherapeutic Agents, 8:903, 1997).

Apoptosis or programmed cell death is the physiological process for the killing and removal of unwanted cells and the mechanism whereby chemotherapeutic agents kill cancer cells. Apoptosis is characterized by distinctive morphological changes within cells that include condensation of nuclear chromatin, cell shrinkage, nuclear disintegration, plasma membrane blebbing, and the formation of membrane-bound apoptotic bodies (Wyllie et al., Int. Rev. Cytol., 68: 251, 1980). The translocation of phosphatidylserine from the inner face of the plasma membrane to the outer face coincides with chromatin condensation and is regarded as a cellular hallmark of apoptosis (Koopman, G. et al., Blood, 84:1415, 1994). The actual mechanism of apoptosis is known to be mediated by the activation of a family of cysteine proteases, known as caspases. However, most prior art anti-cancer therapies are directed to induction of apoptosis, have proven to be less than adequate for clinical applications. Many of these therapies are inefficient or toxic, have adverse side effects, result in development of drug resistance or immunosensitization, and are debilitating for the recipient. Many diseases or conditions are characterized by undesired cellular proliferation and are know to one of ordinary skill in the medical or veterinary arts.

Induction of programmed cell death via the induction of senescence (Dimri et al., Proc. Natl. Acad. Sci USA 92:20, 1995) or apoptosis (Wyllie et al., Int. Rev. Cytol. 68:251, 1980) is important for the treatment of disorders that involve aberrant accumulation of unwanted cells such as, but not limited to, cancer, autoreactive, autoimmune, inflammatory and proliferative disorders. However, most prior art anti-cancer therapies, whether directed to induction of apoptosis or to stimulation of the immune system, have proven to be less than adequate for clinical applications. Many of these therapies are inefficient or toxic, have adverse side effects, result in development of drug resistance or immunosensitization, and are debilitating for the recipient. New methods are needed for evaluating molecules to predict whether they will possess a desired biological activity.

Synthetic oligonucleotides are polyanionic sequences that are internalized in cells (Vlassov et al., Biochim. Biophys. Acta, 11197:95, 1994). Synthetic oligonucleotides are reported that bind selectively to nucleic acids (Wagner, R., Nature, 372:333, 1994), to specific cellular proteins (Bates et al., J. Biol. Chem., 274:26369, 1999) and to specific nuclear proteins (Scaggiante et al., Eur. J. Biochem, 252:207, 1998) in order to inhibit proliferation of cancer cells.

Synthetic 27 base sequences containing guanine (G) and variable amounts of thymine (T) (oligonucleotides GTn) wherein n is $\geq 1$ or $\leq 7$ and wherein the number of bases is $\geq 20$ (Scaggiante et al., Eur. J. Biochem., 252:207, 1998), are reported to inhibit growth of cancer cell lines by sequence specific binding to a 45 kDa nuclear protein, whereas GTn, wherein the number of bases is $\leq 20$, are reported to be inactive against cancer cell lines (Morassutti et al., Nucleosides and Nucleotides, 18:1711, 1999). Two synthetic GT-rich oligonucleotides of 15 and 29 bases with 3' aminoalkyl modifications are reported to form G-quartets that bind to nucleolin and to inhibit proliferation of cancer cell lines (Bates et al., J. Biol. Chem., 274:26369, 1999). The synthetic six base TTAGGG-phosphorothioate, having a sequence identical to that of the mammalian telomere repeat sequence, is reported to inhibit proliferation of Burkitt's lymphoma cells in vitro and in vivo (Mata et al., Toxicol. Applied Pharmacol., 144:189, 1997). However, the synthetic six base TTAGGG-phosphodiester nucleotide is reported to have no anti-telomerase activity (U.S. Pat. No. 5,643,890).

Deoxyribonucleotides with biological activity such as antisense DNA (mRNA binding or triplex-forming DNA) or immunostimulatory CpG motifs are characterized by sequence-specific linear motifs, often stabilized by intramolecular base-pair bonding. Backbone modification, such as phosphorothioate substitution, does not adversely affect and often enhances the activity of these molecules.

We have previously described a composition and method comprising 2 to 20 base 3'-OH, 5'-OH synthetic oligonucleotides selected from the group consisting of $(G_xT_y)_n$, $(T_yG_x)_n$, $a(G_xT_y)_n$, $a(T_yG_x)_n$, $(G_xT_y)_nb$, $(T_yG_x)_nb$, $a(G_xT_y)_nb$, $a(T_yG_x)_nb$, wherein x and y is an integer between 1 and 7, n is an integer between 1 and 12, a and b are one or more As, Cs, Gs or Ts, wherein the sequence is between 2 and 20 bases and wherein the sequence induces a response selected from the group consisting of induction of cell cycle arrest, inhibition of proliferation, induction of caspase activation and induction of apoptosis in a number of cancer cells (PCT CA00/01467, WO 01/44465).

Computational procedures allow a correlation of three dimensional molecular structures with biological activity, and facilitate prediction of the conformation of active molecules. Modeling entails the use of mathematical equations that are capable of representing accurately the phenomenon under study. Molecular mechanics analysis (Allinger, N. L., J. Comput. Chem., 12, 844,1991) can be used to analyze structural and conformational relationships. The fundamental assumption of molecular mechanics is that data determined experimentally for small molecules (bond length, bond angles, etc.) can be extrapolated to larger molecules. Molecular modeling approaches have been used to determine structure activity relationships and to enable the prediction of active three dimensional molecular conformations (N. Evrard-Todeschi et al., J. Chem. Inf. Comput. Sci., 38:742,1998; Chen H. et al., J. Med. Chem. 36:4094, 1993; A. Guama et al., J. Med. Chem., 40:3466,1997; M. Read, et al. Proc. Natl. Acad. Sci. USA, 98:4844, 2001).

Therefore, there is a continuing need for the identification of novel 3-dimensional conformations or structural motifs in oligonucleotides that are useful in predicting their biological activity, particularly with regard to their capability to induce cellular responses in cells. What is needed is the ability to predict cellular responses including responses such as apoptosis in cancer cells.

SUMMARY OF THE INVENTION

The present invention fulfills this need by providing a computer-based method useful for predicting whether oligonucleotide sequences possess apoptotic activity. This in silico method also predicts the relative efficacy of the oligonucleotide sequence to induce apoptosis. This invention provides a rational basis for in silico evaluation or screening of oligonucleotide compositions for their ability to induce apoptosis, thereby providing a means to select specific oligonucleotide compositions for further testing in vivo or in vitro. This invention provides significant savings in the cost of drug design and development by: a) identifying oligonucleotide compositions with specific predicted biological activity; b) predicting the efficacy of the oligonucleotide compositions with the specific predicted biological activity; and, c) reducing the number of candidate oligonucleotide compositions to be tested in vitro and in vivo for apoptotic activity.

Prediction of the capability of a sequence to induce apoptosis is desired in several diseases and conditions including but not limited to the following: cancer; hyperproliferative disorders; autoimmune disease; arthritis; rheumatoid arthritis; inflammation; lymphoproliferative disorders; restenosis of vessels after angioplasty; and, asthma. Prediction of the capability of a sequence to induce apoptosis is particularly desirable in cancers including but not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma and metastases derived therefrom.

The unexpected ability to predict apoptosis-inducing activity in silico with a high degree of precision (>95%) reduces the need for costly high-throughput chemical synthesis and apoptosis-inducing screening, thus enabling the identification of biologically active molecules in a much more efficient and cost effective manner.

An advantage of the present invention is that it accelerates the discovery of new therapeutic compositions. Another advantage of the present invention is that it decreases the cost of discovering new therapeutic compositions by providing candidate oligonucleotide sequences for biological testing in vivo and in vitro. These savings directly affect the cost of therapeutic drugs for patients and throughout the health care industry for humans and animals. Still another advantage of the present invention is that it decreases the cost of discovering new therapeutic compositions by predicting the efficacy of oligonucleotide sequences, thereby providing a prioritization for biological testing in vivo and in vitro.

Accordingly, it is an object of the present invention is to provide a computer-based method useful for evaluation of oligonucleotide sequences.

It is another object of the present invention to provide a computer-based method useful for evaluation of oligonucleotide sequences to predict whether they possess the ability to induce a response in a cell such as inhibition of cellular proliferation, induction of cell cycle arrest or induction of apoptosis.

It is a specific object of the present invention to provide a computer-based method useful for evaluation of oligonucleotide sequences to predict whether they possess the ability to induce apoptosis in cells.

Yet another object of the present invention is to provide a computer-based method useful for evaluation of oligonucleotide sequences to predict whether they possess the ability to induce apoptosis in cancer cells.

Yet another object to the present invention is to provide a method useful for identifying oligonucleotide sequences that will be useful in the treatment of disease.

Another object to the present invention is to provide a method useful for identifying oligonucleotide sequences that will be useful in the treatment of diseases and conditions characterized by undesired cellular proliferation.

Still another object to the present invention is to provide a method useful for identifying oligonucleotide sequences that will be useful in the treatment of diseases and conditions characterized by undesired cellular proliferation such as autoimmune disease, inflammation, arthritis, asthma, restenosis of vessels after angioplasty, hyperproliferative disorders, lymphoproliferative disease, and cancer.

Yet another object to the present invention is to provide a method useful for identifying oligonucleotide sequences that will be useful in the treatment of cancer.

Another object to the present invention is to provide a method that allows the identification of molecules with apoptosis-inducing activity in silico without resort to high throughput chemical synthesis and biological activity screening.

The unexpected and surprising ability of the present invention to predict the capability and efficacy of an oligonucleotide sequences to induce a cellular response, and particularly to inhibit cell proliferation, to arrest the cell cycle progression and/or to induce apoptosis in cells addresses a long unfulfilled need in the medical arts and provides an important benefit for animals and humans.

These and other objects, features and advantages of the present invention will become apparent after a review of the following detailed description of the disclosed embodiment and the appended claims.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 2b. Schematic representation of framed centrum of electronegativity in three dimensions showing x, y, z, alpha (α) and beta (β) variables as defined in the specification and the 5' and 3' orientation. Also shown are areas of electronegativity from phosphate groups, areas of electropositivity from amines and amido groups, phosphates, deoxyribose, and bases.

Figure 1:
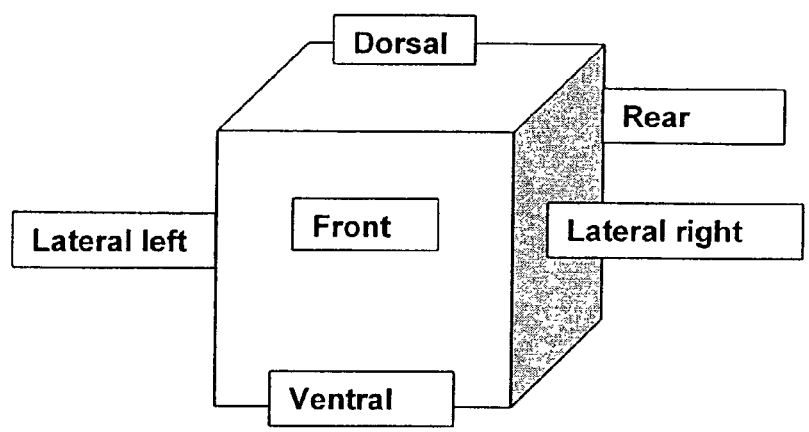
FIG. 1. Spatial definition of the general orientation of a centrum in three dimensions (front, rear, ventral, dorsal, lateral left and lateral right.

The first position is presented twice as a solid, black and white picture and as a color picture with dots as the solvent accessible surface. The hydrogen atoms are suppressed for better clarity. The following colors are used to represent the atoms in the 3-dimensional sequences shown in the figures: Blue=nitrogen; Grey=carbon; Pink=phosphorus; Red=oxygen; Yellow=sulfur. The four rotational views (a, b, c, and d) are provided as examples to demonstrate the globular nature of the centrum in different orientations.

FIG. 3. TGT
FIG. 4. GGGGGG
FIG. 5. GGGTGG phosphorothiote backbone
FIG. 6. GGG
FIG. 7. TTGTGG
FIG. 8. GGGTGGGG
FIG. 9. GGGTGG$_{13}$ 3P(3'-phospate)
FIG. 10. 5P$_{13}$ GGGAGG(5'-phosphate)
FIG. 11. 5P$_{13}$ GGGTGG(5'-phosphate)
FIG. 12. GGGTGG
FIG. 13. GGGGTGG

DETAILED DESCRIPTION OF THE INVENTION

The present invention provides a computer-based method useful for predicting whether oligonucleotide sequences possess the ability to induce a cellular response, and particularly to inhibit cell proliferation, to arrest the cell cycle progression and/or to induce apoptosis in cells. In a preferred embodiment, this in silico method predicts whether oligonucleotide sequences possess the ability to induce apoptosis. This in silico method also predicts the relative efficacy of the oligonucleotide sequence to induce a cellular response, and particularly to inhibit cell proliferation, to arrest the cell cycle progression and/or to induce apoptosis in cells. In a preferred embodiment, this in silico method predicts the relative efficacy of the oligonucleotide sequence to induce apoptosis in cells. This invention provides a rational basis for in silico evaluation or screening of oligonucleotide compositions to predict their ability to inhibit cell proliferation, to arrest the cell cycle progression, to activate caspases, to cleave PARP, and/or to induce apoptosis in cells, thereby providing a means to select specific oligonucleotide compositions for further testing in vivo or in vitro.

The method of the present invention is used to determine whether an oligonucleotide sequence possesses one or more centrums which are useful in predicting whether the sequence has apoptotic biological activity.

As used herein, sequence refers to an association of bases, deoxyribose and phosphodiester groups in an oligonucleotide sequence forming an identifiable globular 3-dimensional structure (that is based on the centrum of negatively charged phosphate groups framed by positive charges of amino/amido groups of bases at the opposite side) that is used to predict the capability of the sequence to induce apoptosis in cells.

As used herein, "centrum" refers to the absence or presence of intramolecular substructure comprising two or more phosphate groups and two or more adjacent bases (Type A centrum) or non-adjacent bases (Type B centrum), with or without stabilizing intermolecular hydrogen bonding. The centrum is defined as adjacent (type A) if bases are adjacent with a perpendicular orientation in the same or opposite plane to the phosphate necklace. The centrum is defined as non-adjacent (type B) if the order of the bases is not consecutive. A preferred orientation is type A or B, a more preferred orientation is type A and B, a most preferred orientation is type A with the bases in the same plane perpendicular to the phosphate necklace. If a sequence has one centrum at the 5' end and a second centrum at the 3' end then the subscript index, e.g. $A_1$ refers to the type A centrum at the 5' end. The subscript $A_2$ refers to the type A centrum at the 3' end. The same indexing is applied to the type B centrum. The centrum is considered as framed if there is presence of amino or amido or both groups at the opposite sites of the phosphate necklace.

The following notation is used to describe the sequence of bases in the oligonucleotide sequences: A=Adenine; C=Cytosine; G=Guanine; T=Thymine.

The following parameters are used in describing the 3-dimensional oligonucleotide sequences: A) All distances are in pm; B) Intramolecular hydrogen bonds are assumed to form if the mutual distance of participating atoms is less than 300 pm; and, C) The molecular dynamics values are in kcal/mole.

As used herein, a cellular response refers generally to inhibition of proliferation, to arrest in cell cycle progression and/or to induction of apoptosis in cells. A preferred response is induction of apoptosis. Cells include any cell, particularly cells exhibiting undesired proliferation. Such cells may be found in hyperproliferative disorders; autoimmune disease; arthritis; rheumatoid arthritis; inflammation; lymphoproliferative disorders; cancer; and, asthma. Cancer cells include, but are not limited to, cells from squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, or lymphoma and metastases derived therefrom.

As used herein, the phrases "therapeutic treatment" and "amount effective to" refer to an amount of a 3-dimensional oligonucleotide sequence effective to inhibit cell proliferation, arrest the cell cycle progression or induce apoptosis in cells, including cancer cells.

Administration of a composition comprising an effective amount of a oligonucleotide sequence of the present invention to an animal, including a human, is a therapeutic treatment that prevents, treats or eliminates a disease, including, but not limited to, cancer, arthritis, rheumatoid arthritis, hyperproliferative disorders, restenosis of vessels after angioplasty, lymphoproliferative disorders and asthma.

Induction of apoptosis is particularly desirable in cancers including but not limited to, squamous cell carcinoma, fibrosarcoma, sarcoid carcinoma, melanoma, mammary cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma and metastases derived therefrom.

Although not wanting to be bound by the following statement, it is proposed that a molecular combination in an oligonucleotide sequence of negative charges or electronegativity (from for example phosphate groups), positive charges or electropositivity (from for example amine and amido groups), in conjunction with appropriate intra-molecular hydrogen bonding and inter-atomic dimensions as defined herein, will possess the ability to induce apoptosis in cancer cells.

Computer Hardware and Software

It is to be understood that the present invention may be practiced using any computer with sufficient memory and computing speed to operate chemical drawing software used by those of ordinary skill in the art and to measure the parameters of the centrum. Measurements of the various parameters of the centrum are accomplished by means of the software translates drawn structures into 3-d structures.

Using the software, interatomic distances are measured in pm (picometers) in the 3-dimensional structure where the first atom is selected and at the tip of the cursor (pointer) the information about the distance between those atoms is shown.

Further, any chemical software that facilitates determination of the components of the centrum described below may be used. Such software is commonly known to those of ordinary skill in the art. In one embodiment of the present invention, ChemDraw software is employed. The Chem3D software is supplied by Cambridgesoft.Com, Cambridge, Mass., USA. Other software packages known to one of ordinary skill in the art of molecular modeling may be employed, such as Sybill (from Tripos), Charm and Inside II (from Accelrys).

The method of the present invention may be practiced using personal computers such as commonly available to consumers, for example, desktop units and laptops manufactured by Dell, Apple, Compaq, Hewlett-Packard, Gateway, IBM or more sophisticated computers such as Silicon Graphics or Cray computers.

The computer is operationally connected to a means for entry of information, such as a keyboard, touchscreen or other entry device known to one of skill in the art. The computer is operationally connected to means such as CD read write devices, disk drive or other means known to one of skill in the art for accessing and inputting information. Further, computer may be operationally connected to the internet, to remote databases, or to other servers that provide access to databases of chemical structures so that information concerning specific molecular structures may be obtained rapidly.

The computer is operationally connected to a means for display or output of information, such as monitors, printers and other display means known to one of skill in the art. Such means permit visualization of three dimensional structure of oligonucleotide sequences and various parameters associated with their structure, such as globular shape, shape of the phosphate backbone orientation and location of phosphate groups, 2-deoxyribose, purines, pyrimidines, amino groups, amido groups, hydroxyl groups at 3' and 5' ends, and centrums.

General Method of the Invention for in Silico Identification of Centra in Oligonucleotides The following steps describe the general method of the present invention for identifying centra in an oligonucleotide sequence.

1) Draw the molecule. The oligonucleotide molecule was drawn using ChemDraw v.5 software
2) Check for errors Structures were examined to ensure that the atoms, bonds and valences were correct.
3) Translation and analysis of drawn model by Chem3D software. The structure was drawn and then opened using the Chem3D software structure to create a 3-dimensional model. If an error was found (e.g., double bonds instead of single bonds) a warning message was generated indicating that something was not correct. In such case the ChemDraw program was used to make changes in the drawn structure, and the procedure was repeated by opening the drawn (corrected) structure in Chem3D software.
4) Minimization of energy. Minimization of energy was required for locating stable conformations. From the MM2 menu in CHem3D software, the "Minimize energy" choice was made. The default value of 0.1000 was a reasonable compromise between accuracy and speed. The result contained the values of the following parameters: bond stretching energy; angle bending energy; torsional energy; non-bonded energy; van der Waals energy; electrostatic energy; dipole/dipole contribution; dipole/charge contribution; out-of-plane bending; and, stretch-bend parameters. The stretch-bend parameters are force constants for the stretch-bend interaction terms in the prior list of elements. Parameters are already installed as a part of the software. X and y represent any non-hydrogen atom. when an angle is compressed, the MM2 force field uses the stretch-bend force constants to lengthen the bonds from the central atom in the angle to the other two atoms in the angle.

The Total Steric Energy for the given conformation is expressed a summary of the values mentioned above (bond stretching energy, angle bending energy, torsion energy, van der Waals energy, electrostatic energy and stretch-bend energy) in units of kcal/mol. Stretch bend cross terms are used when a coupling occurs between bond stretching and angle bending. The sum of these energies gives the resulting total steric energy.

5) Calculation of molecular dynamics of molecule at 310° K Molecular Dynamics calculations used Newtonian mechanics to simulate motion of atoms, adding or subtracting kinetic energy as the model moves from lower to higher temperature or vice versa.

The Molecular Dynamics was computed from the Menu MM2 by choosing Molecular Dynamics. The present computation used the default parameters as follows: step interval: 2fs; frame interval: 10 femtosecond (fs); terminate after: 10,000 steps; heating/cooling rate: 1 kcal/atom/1 picosecond (ps); target temperature set at 300° Kelvin (K).

The target temperature was set at 300° K after a set of experiments to determine variance between 300° K and 310° K with respect to the shape of molecules and the temperature range of each molecule. It was found that the default value of 300° K covered the range of the temperature up to 310° K (300° K corresponded to the temperature of 37° C. at which the experiments were performed). It was observed that if the temperature was set to 310° K the range of calculated values usually exceeded the 310° K range.

6) Display of solvent accessible surface to identify molecular conformation, base fingers and necks between them, and to identify globular or linear domains of given molecule. Solvent accessible surface displays provide information about entire molecules instead of specific atom and bond information. The solvent accessible surface represents the portion of the molecule that solvent molecules can access. Common solvents have different values of radius. The default value of water (140 pm) was used. Surfaces display information about the molecule's physical and chemical properties. Surfaces display aspects of the external surface interface (or electron distribution) of a molecule. Molecular surface types are solid, wire mesh, dots, or translucent. To display the molecular surfaces the View menu was employed with four choices: A) solid the surface is displayed as an opaque form. This was useful to examine details of the surface itself and not particularly in the underlying atoms and bonds. B) Wire mesh was displayed as a connected net of lines. The wire mesh displays surface features and permits visibility of the atoms and bonds. C) Dots were displayed as a series of unconnected dots. This was we used to view the underlying structure. D) Translucent surface is displayed in solid form but is partially transparent so that the atoms and bonds are visible.

7) Identification of intramolecular hydrogen bonds. Hydrogen bonds are capable of being formed if the distance is equal to or less than 300 pm.

8) Identification of the presence of phosphate groups forming a phosphate necklace or bead-like appearance as the basis for the formation of a strong electronegative centrum. If a phosphate necklace was present, the size of the centrum was calculated.

9) Determination of the spatial orientation of bases for electropositive framing with respect to phosphate groups in an electronegative centrum.

10) Measurement of interatomic distances of amino/amido groups, and 3' and 5' hydroxyl groups from phosphate groups. Using the software, interatomic distances were measured in pm (picometers) in the 3-dimensional structure where the first atom is selected and at the tip of the cursor (pointer) the information about the distance between those atoms is shown. Interatomic distances: The relative position of each atom in our models was determined by a set of measurements called internal coordinates of Z-matrix. The internal coordinates for any particular atom consists of measurements, in the present case bond length between it and other atoms (more detailed analyses optionally include bond angles and dihedral angles).

Internal coordinate values were obtained by choosing values from the tools menu, pointing to show model tables, and then choosing internal coordinates). The first three atoms in a Z-matrix were defined as follows: 1) the origin atom was the first atom in Z-matrix, and all other atoms in the model were positioned in terms of this atom; 2) the first positioned atom was positioned only in terms of the origin atom. The first positioned atom position was specified by the distance from the origin atom; (in the present case it was the measurement of interatomic distances between phosphate groups, between phosphate groups and amino/amido groups, and between amino/amido groups of involved bases); 3) The second positioned atom is positioned in terms of the origin atom and the first positioned atom. the entire set of internal coordinates was obtained from the tools menu by pointing to show model table and choosing internal coordinates.

11) Comparison of model prediction with actual degree of apoptosis-induction.

A comparison was made of the globular or linear shape and interatomic distances of the electronegative centrum framed by amino/amido groups, and measured apoptotic activity.

12) If two centra were found, then there is a high probability of a higher degree of apoptosis-induction.

Description of Electronegative Centrum Framed by Amino/Amido Groups of Bases as well as by Hydroxyl Groups at 5' and 3' ends.

Figure 2A:
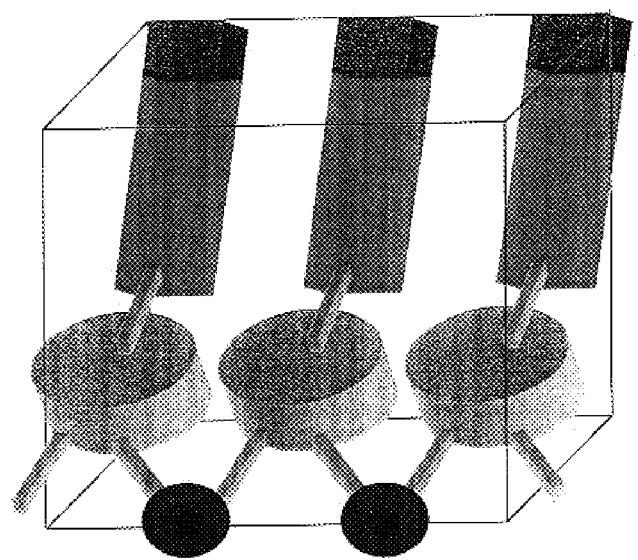
FIG. 2a. Schematic representation of framed centrum of electronegativity in three dimensions.
Figure 3A:
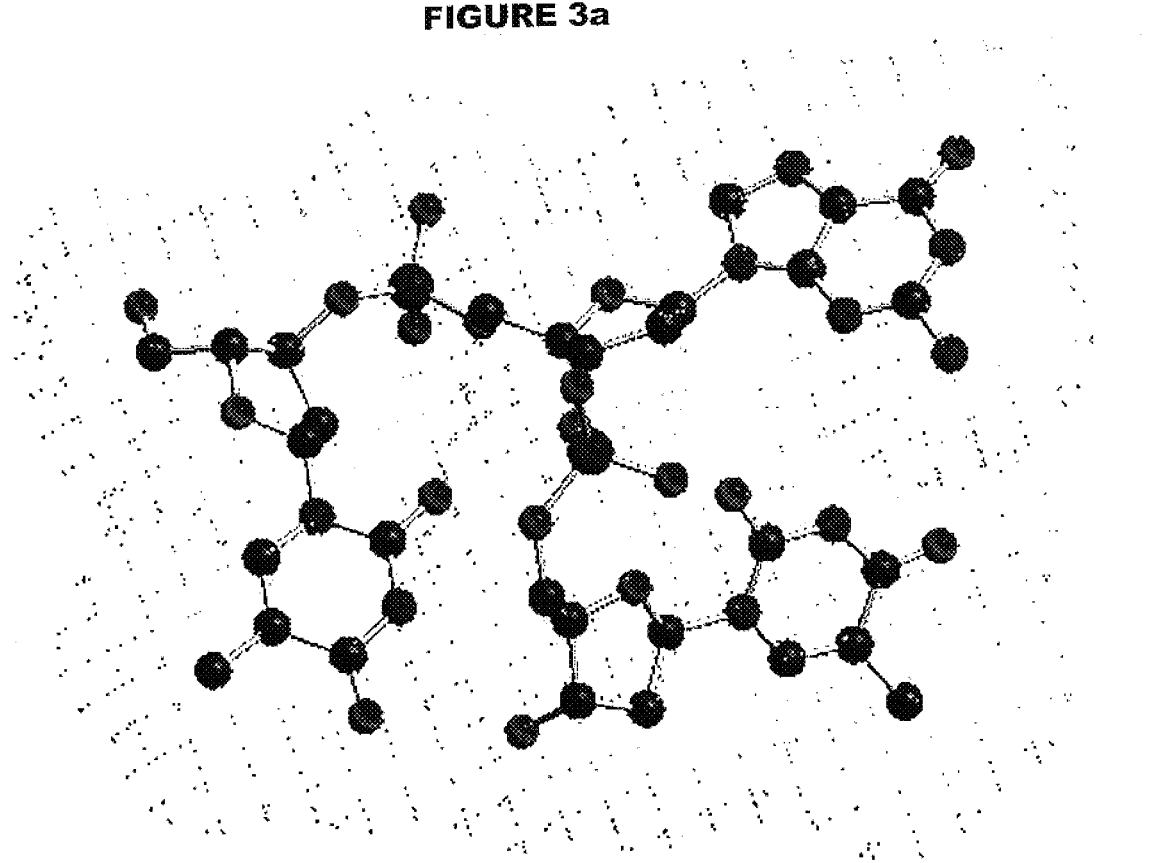
FIGS. 3–13. The following FIGS. 3–13 each consist of views as follows:
a) Position 1 as starting position
b) Position 2 after 90° rotation along the x-axis from the starting position
c) Position 3 after 180° rotation along the x-axis from the starting position
d) Position 4 after 270° rotation along the x-axis from the starting position
e) Position 1 as starting position in black and white showing the solvent accessible surface.
Figure 3B:
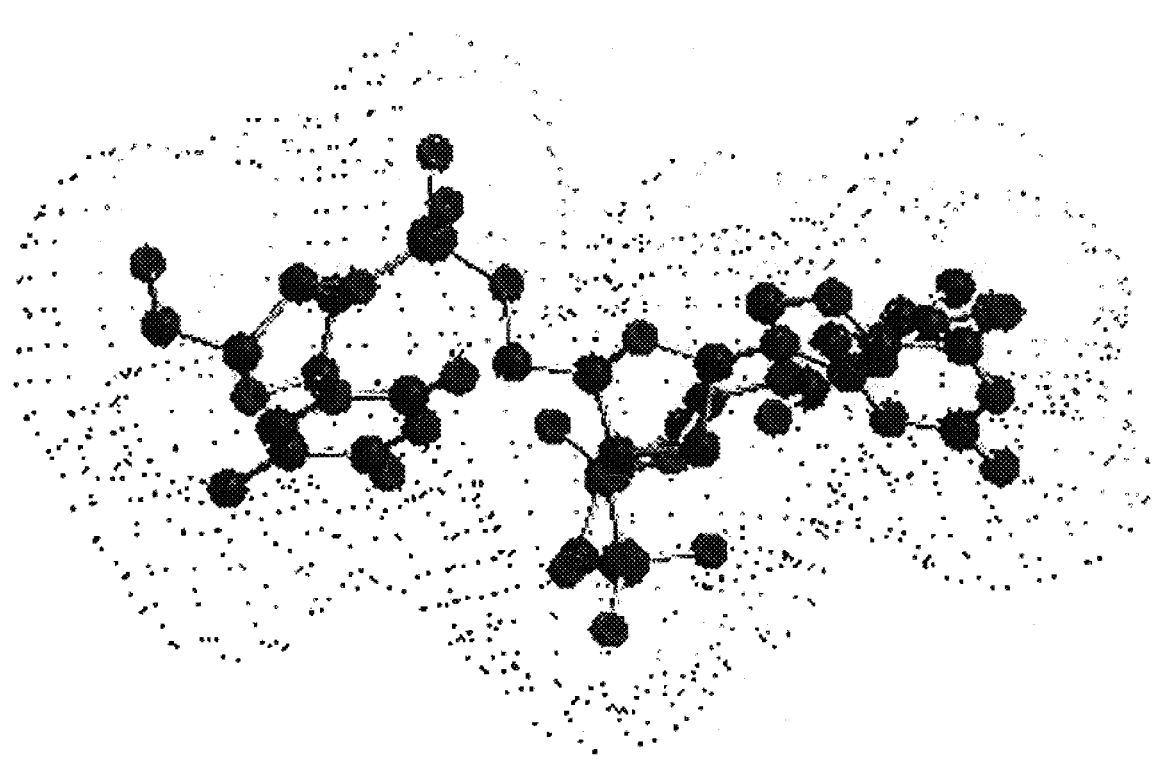
Figure 3C:
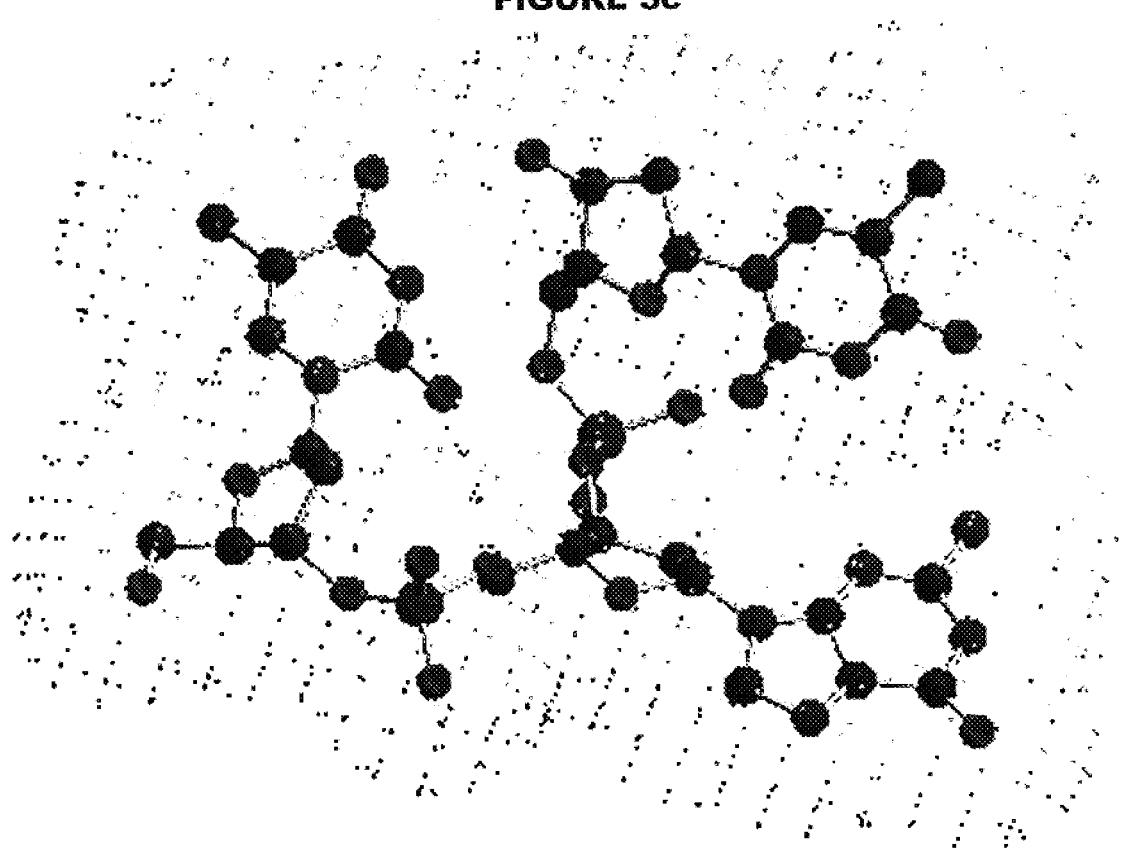
Figure 3D:
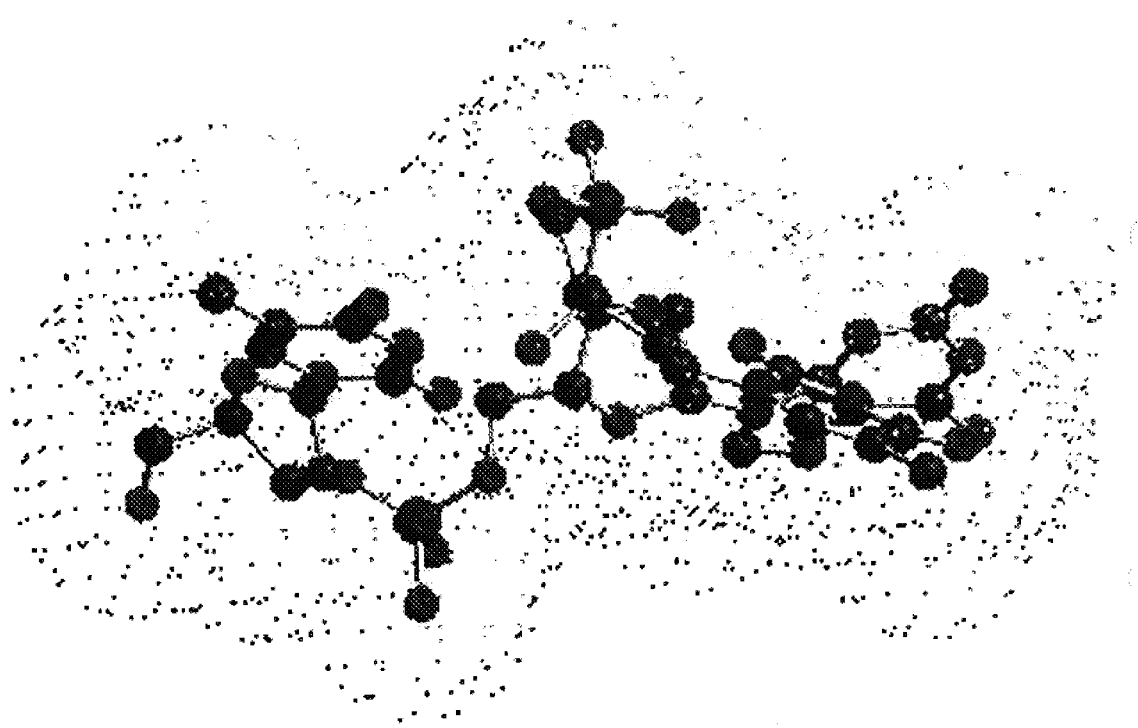
Figure 3E:
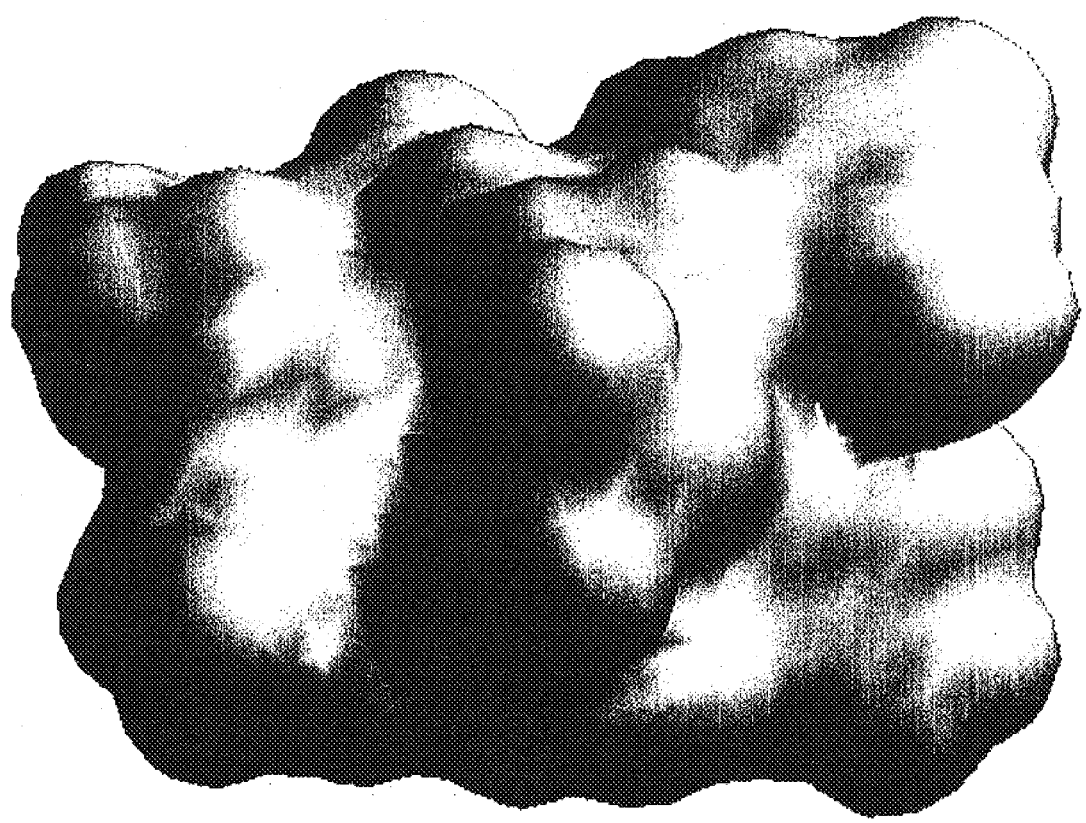
Figure 4A:
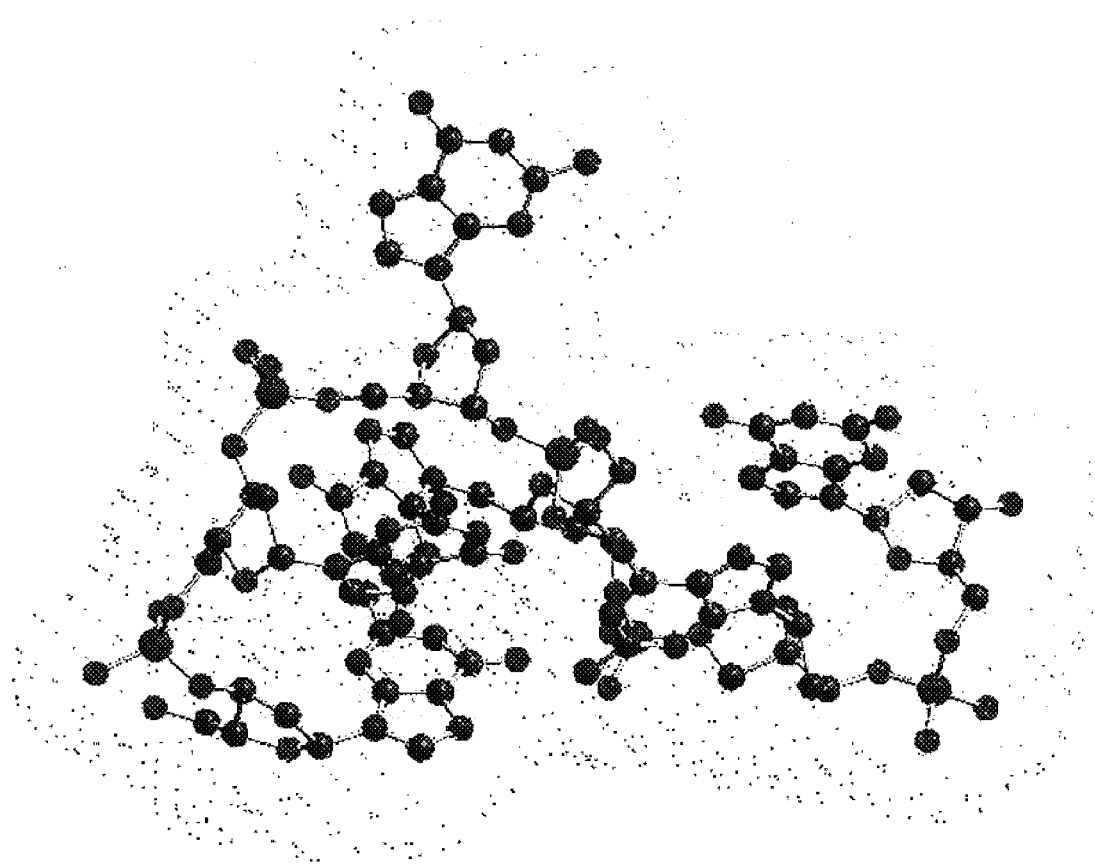
Figure 4B:
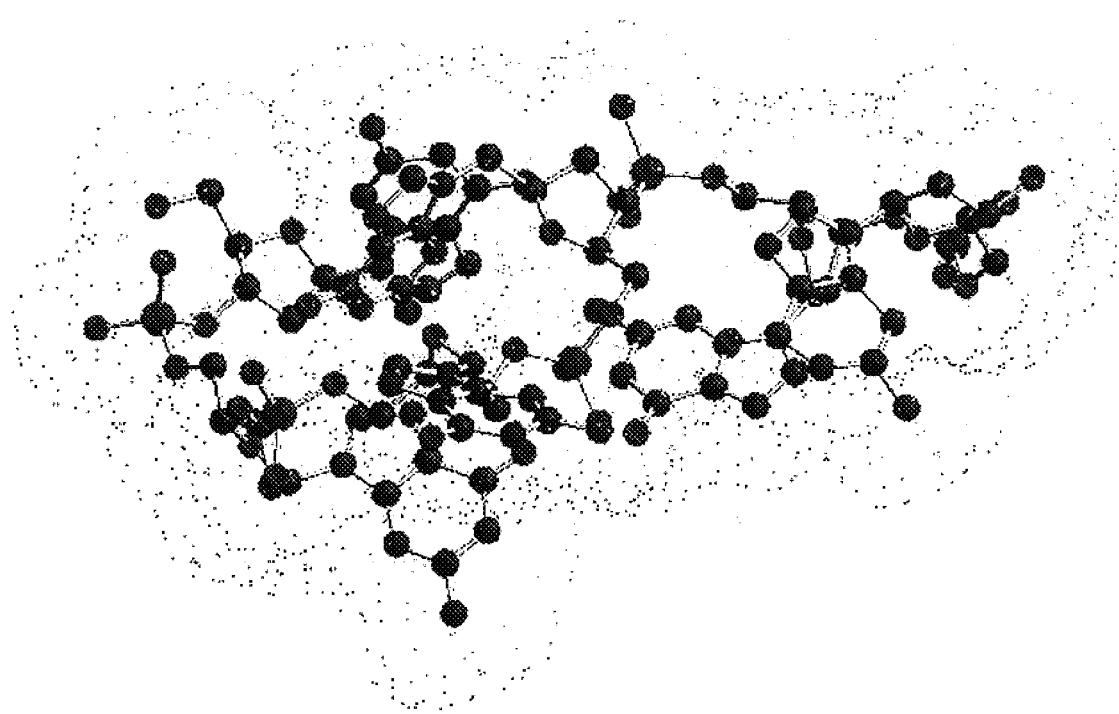
Figure 4C:
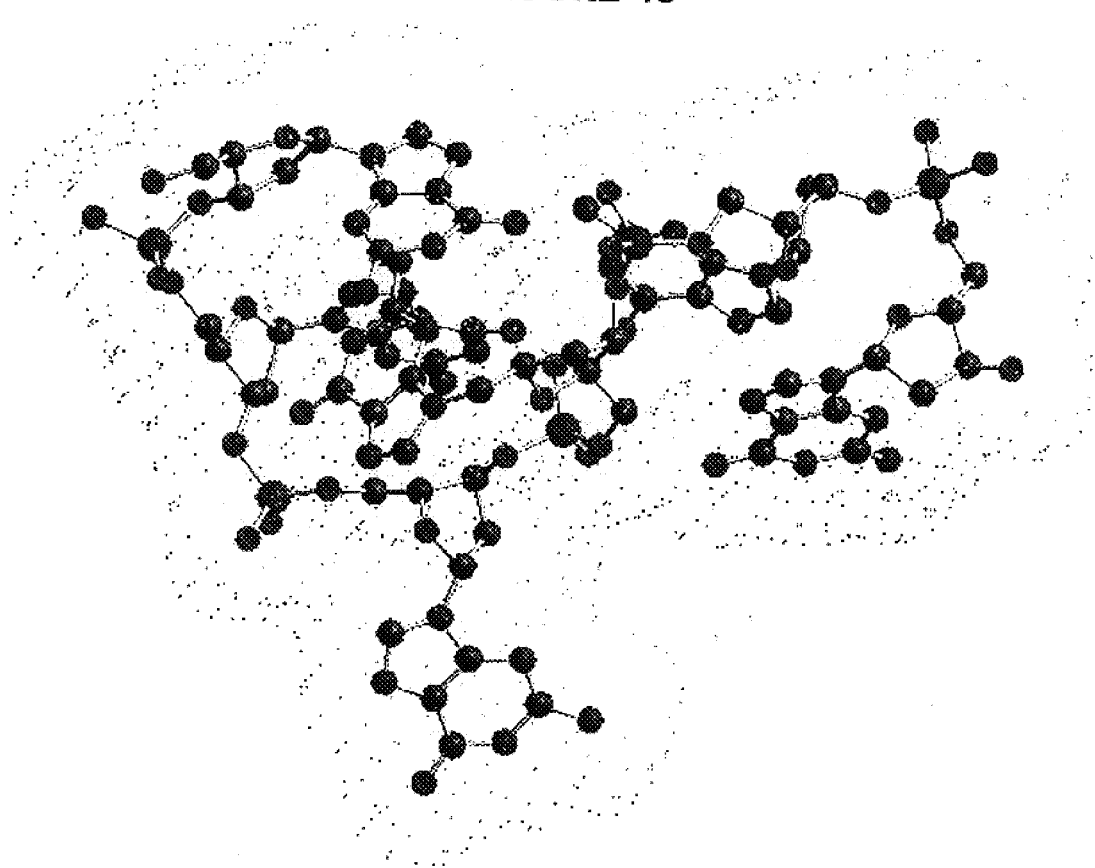
Figure 4D:
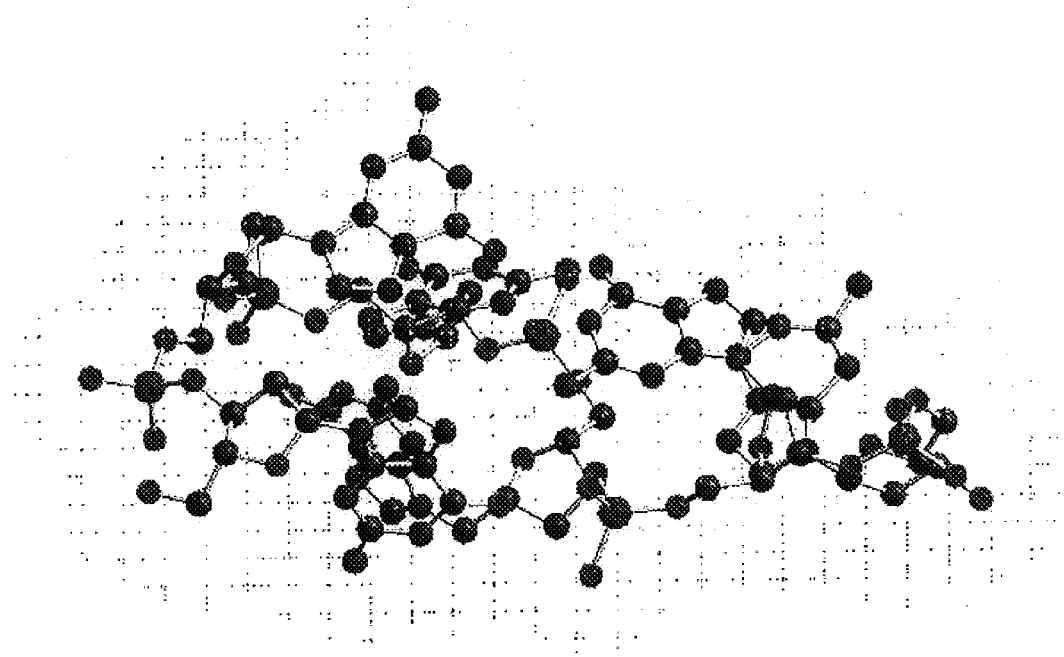
Figure 4E:
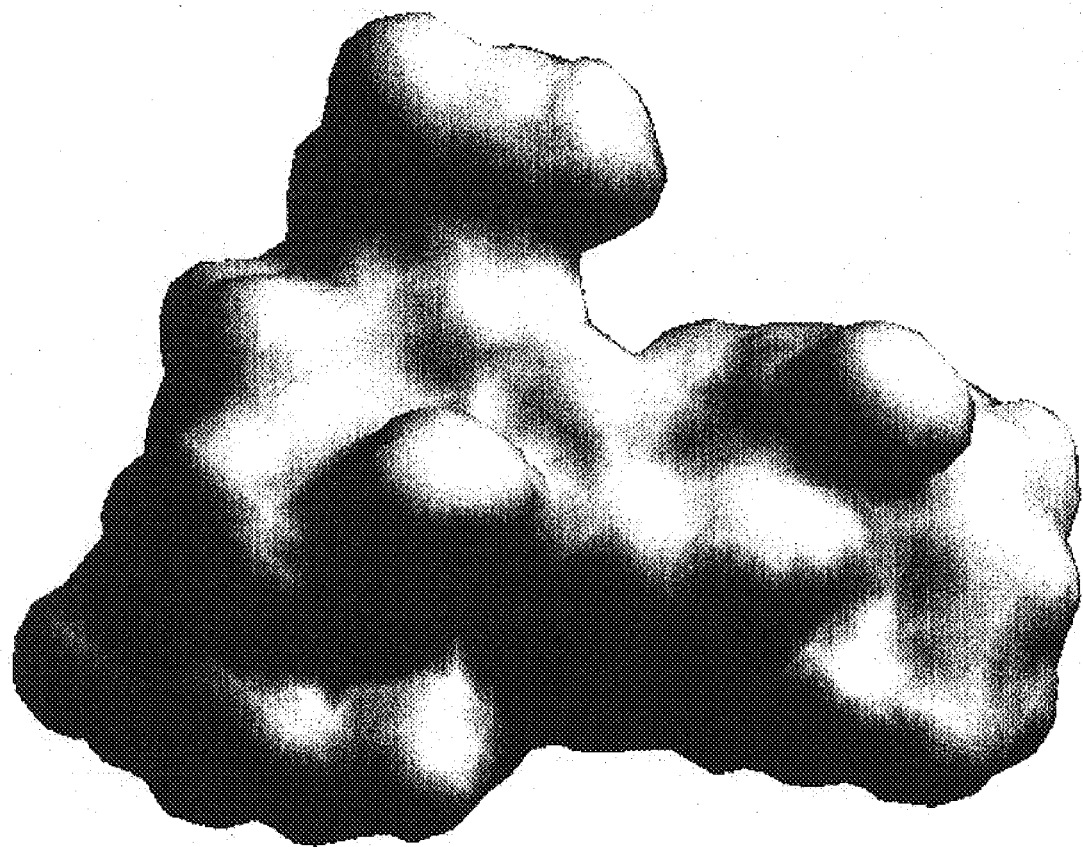
Figure 5A:
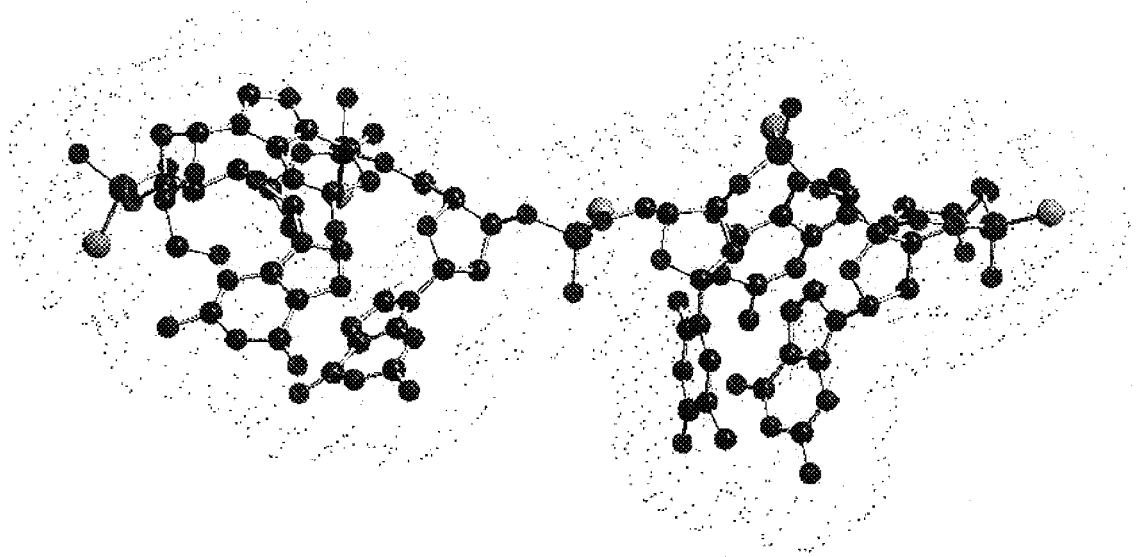
Figure 5B:
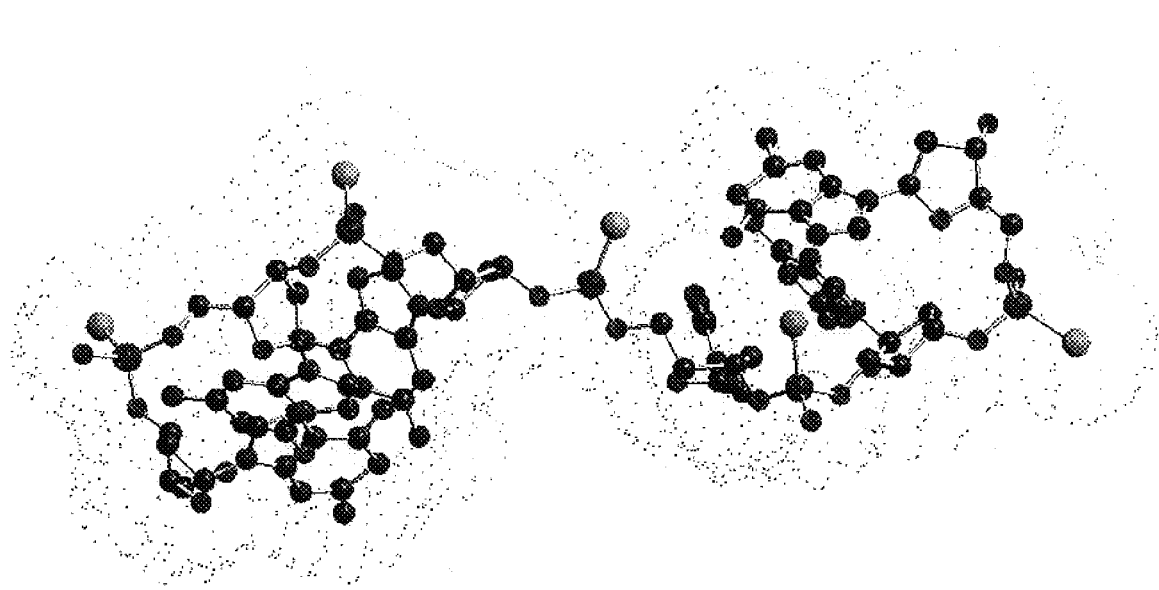
Figure 5C:
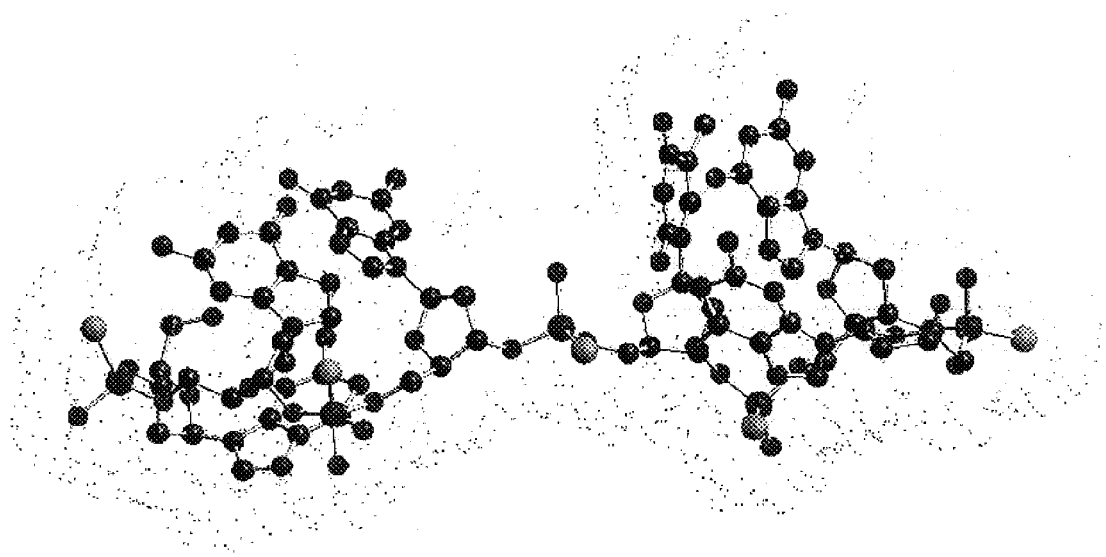
Figure 5D:
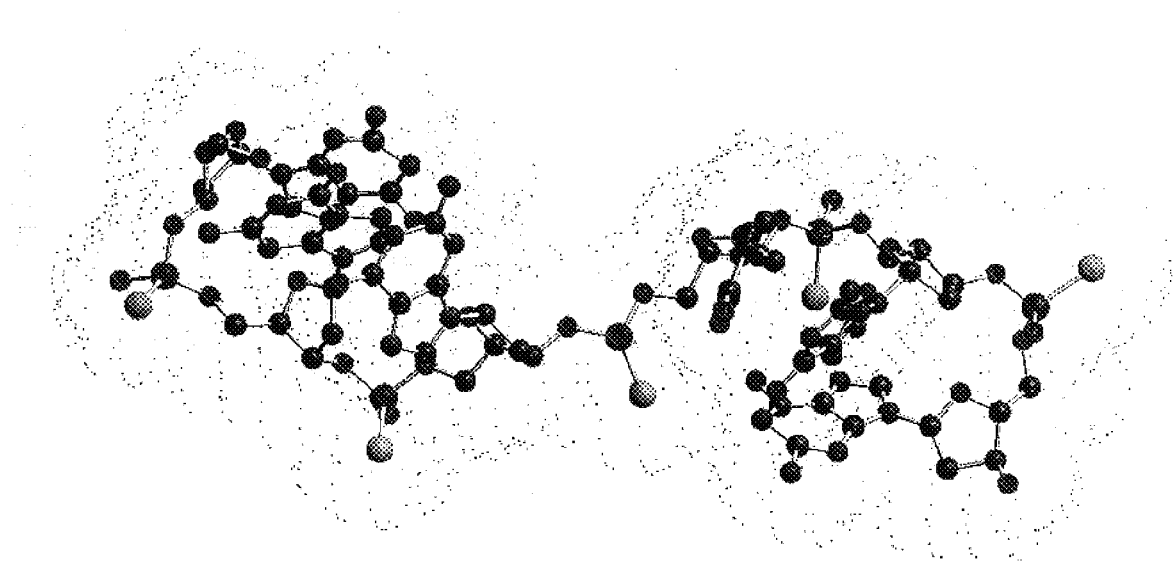
Figure 5E:
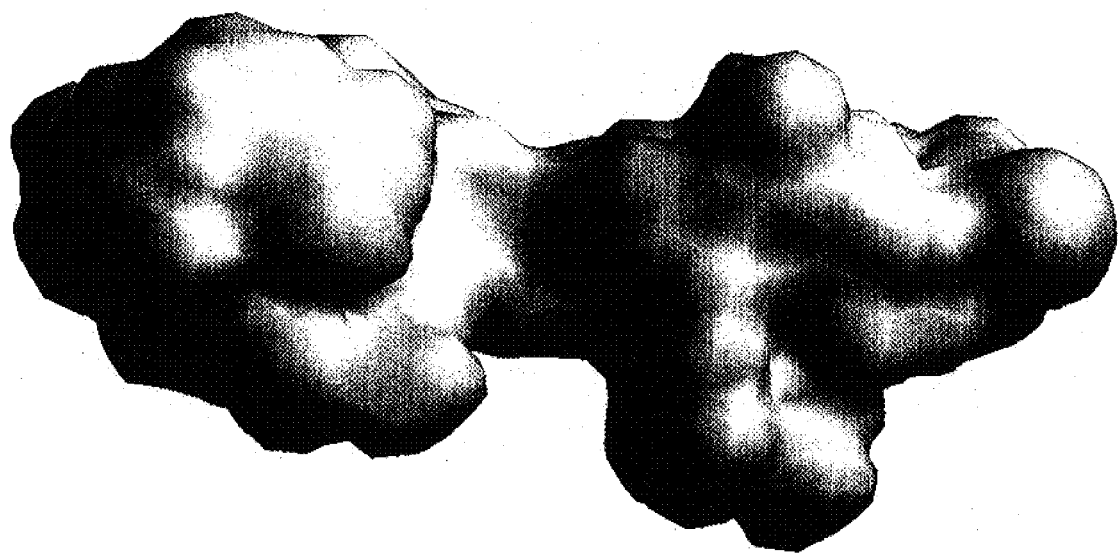
Figure 6A:
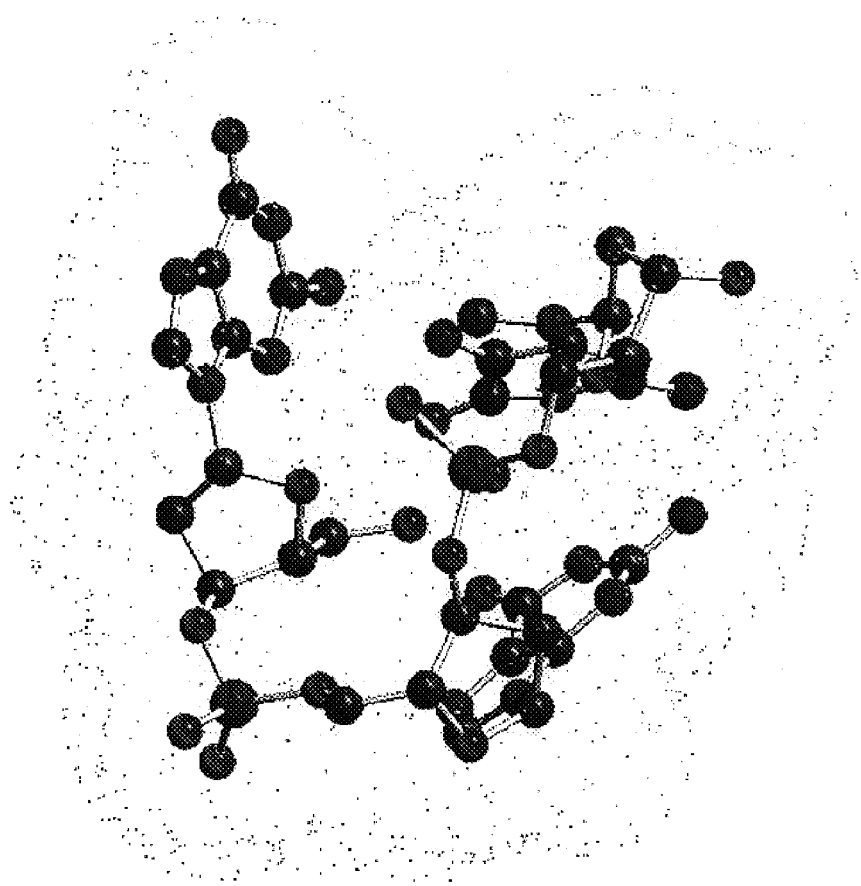
Figure 6B:
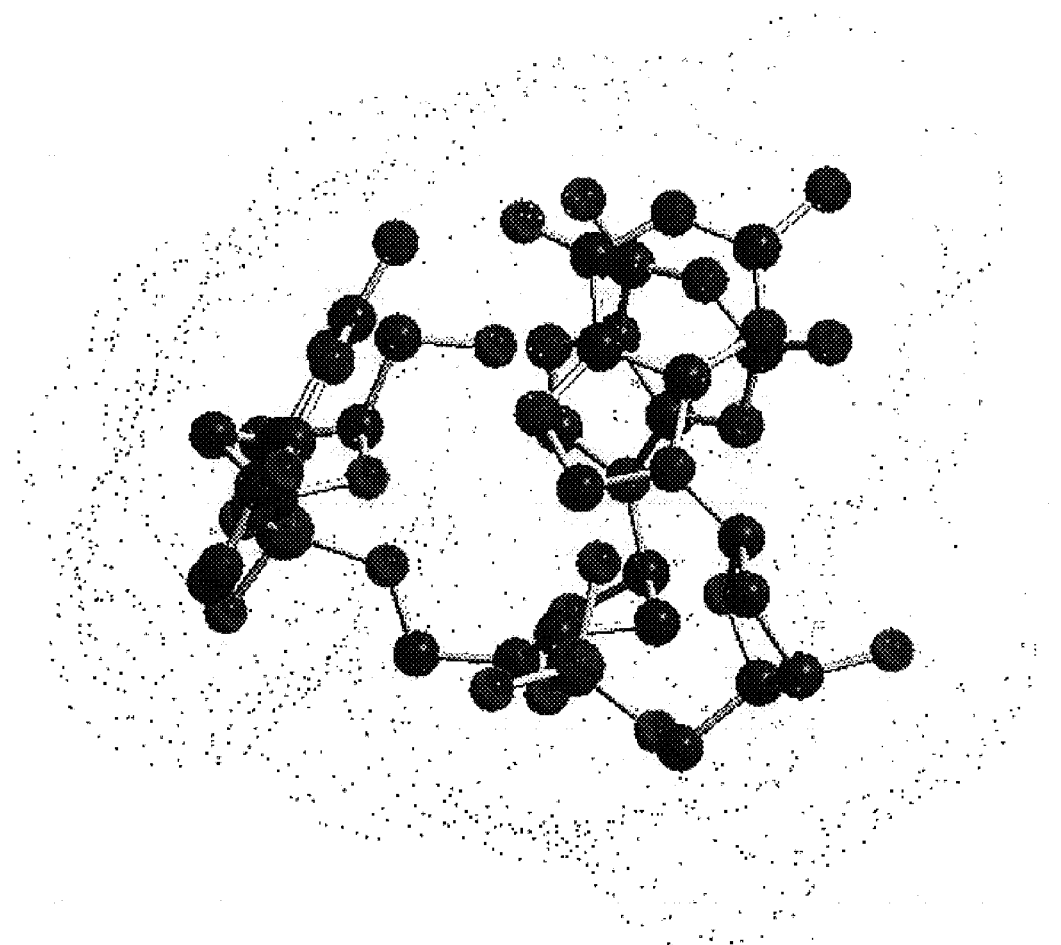
Figure 6C:
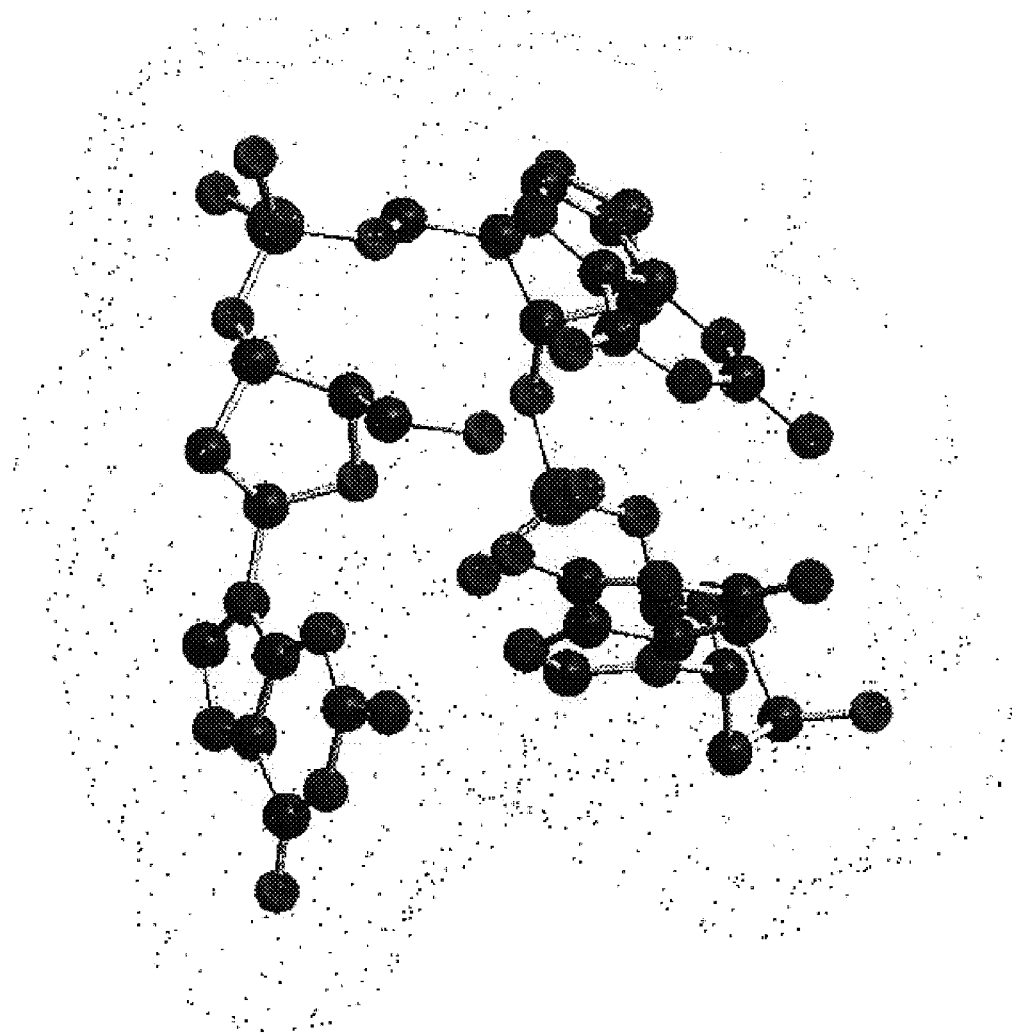
Figure 6D:
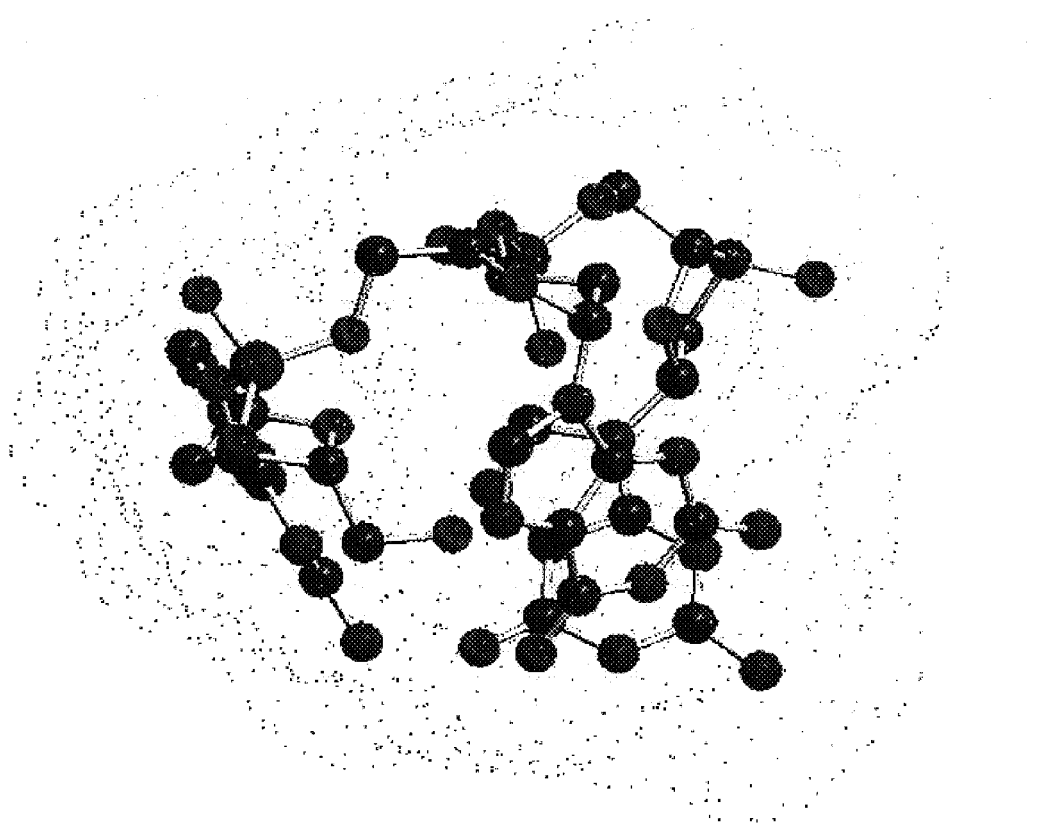
Figure 6E:
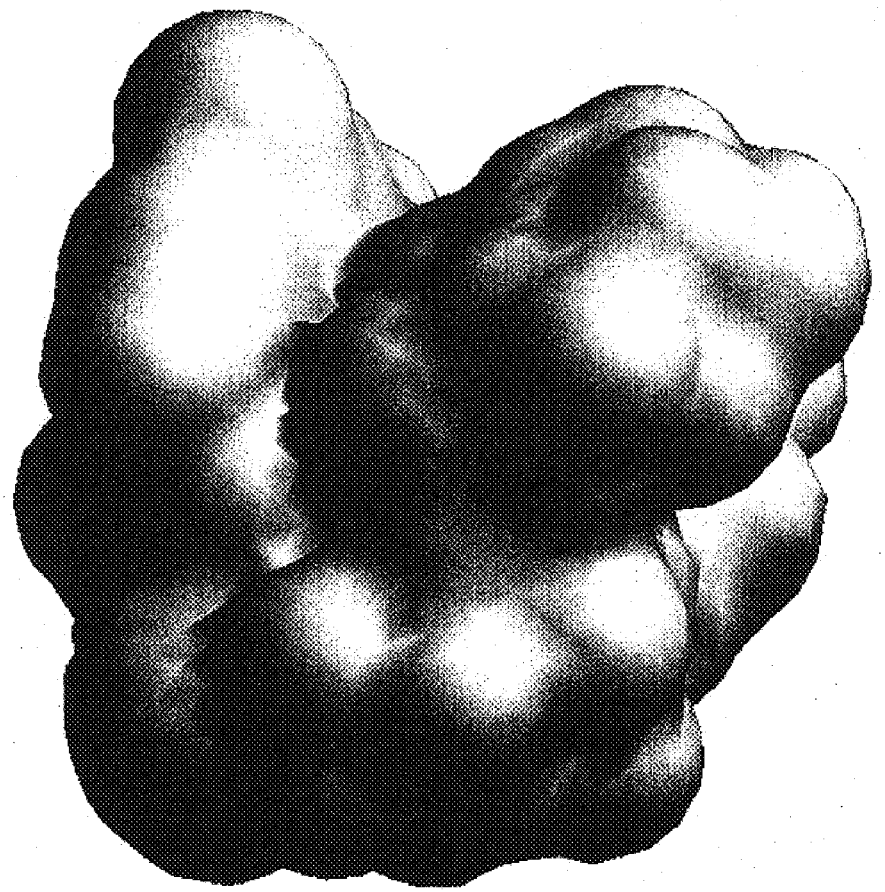
Figure 7A:
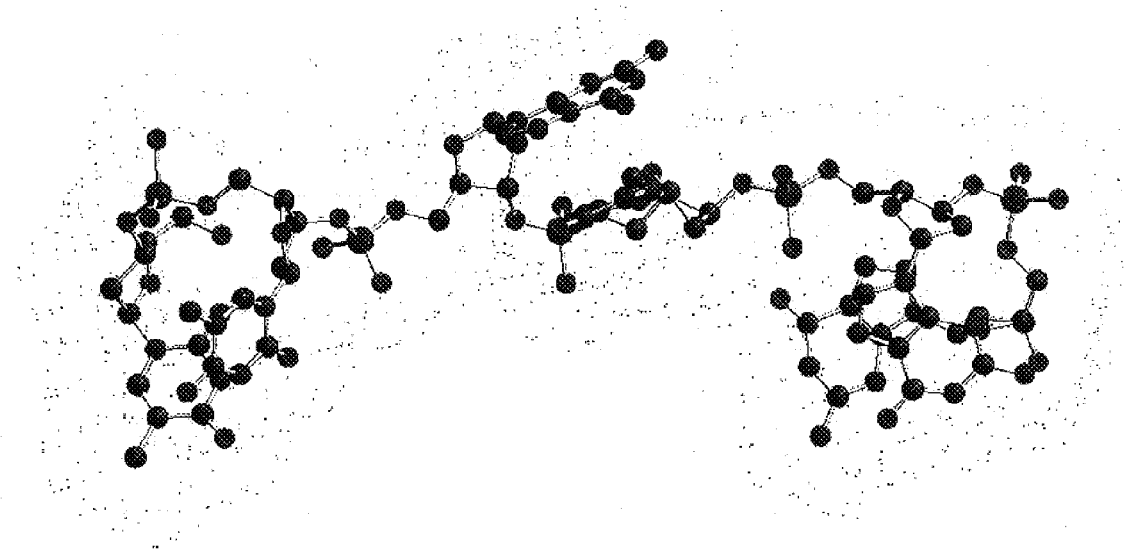
Figure 7B:
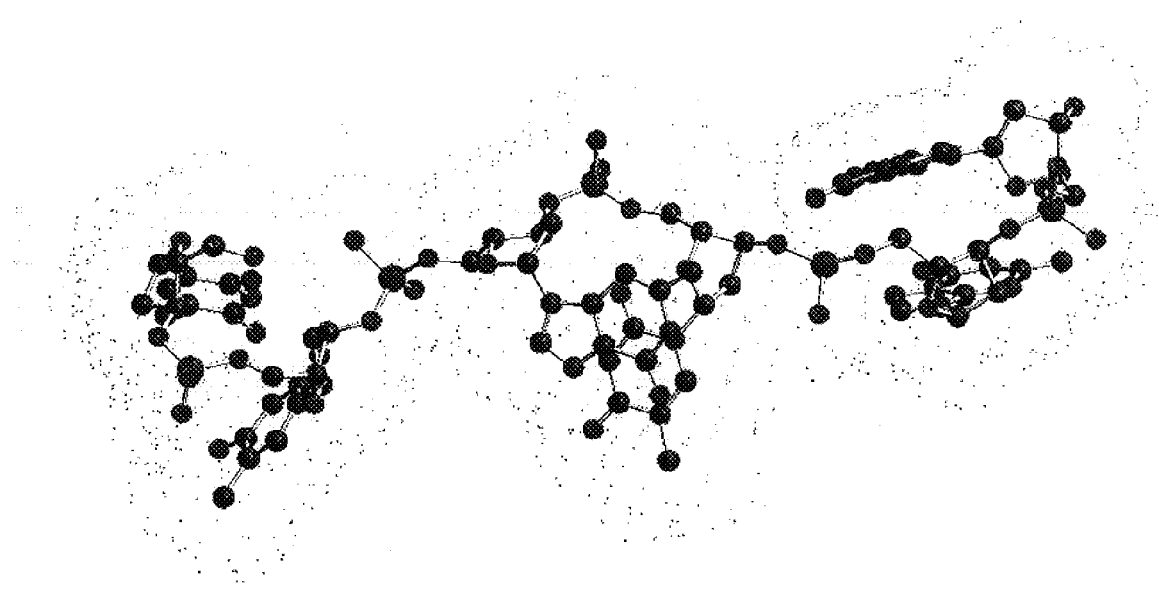
Figure 7C:
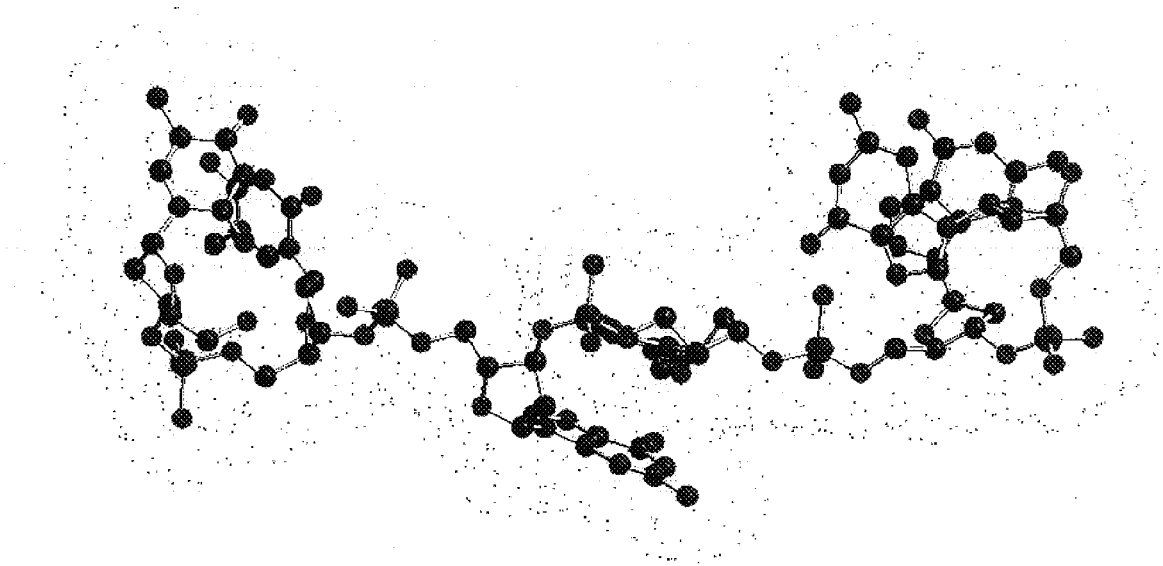
Figure 7D:
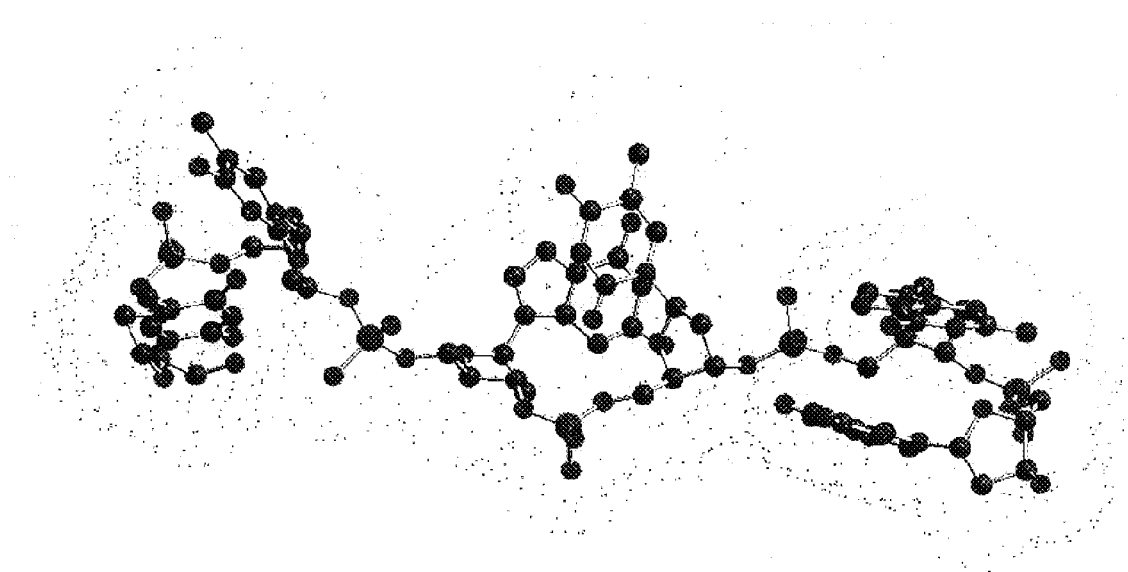
Figure 7E:
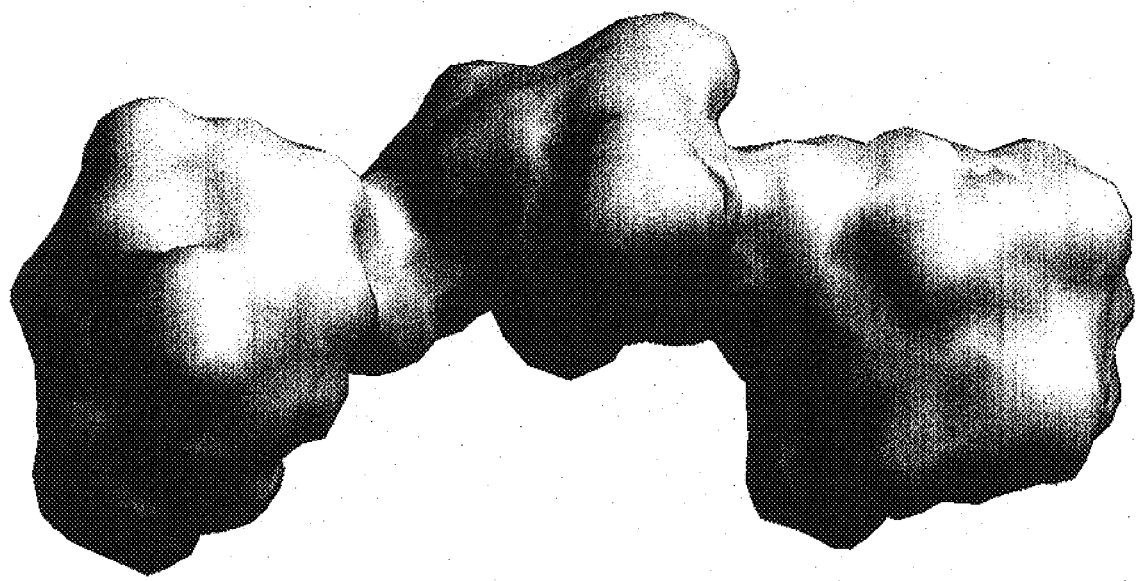
Figure 8A:
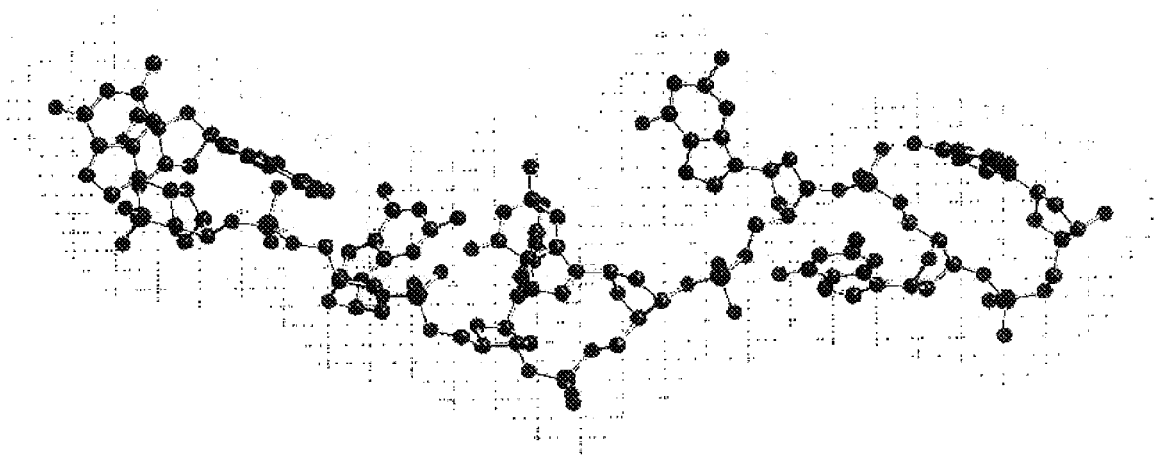
Figure 8B:
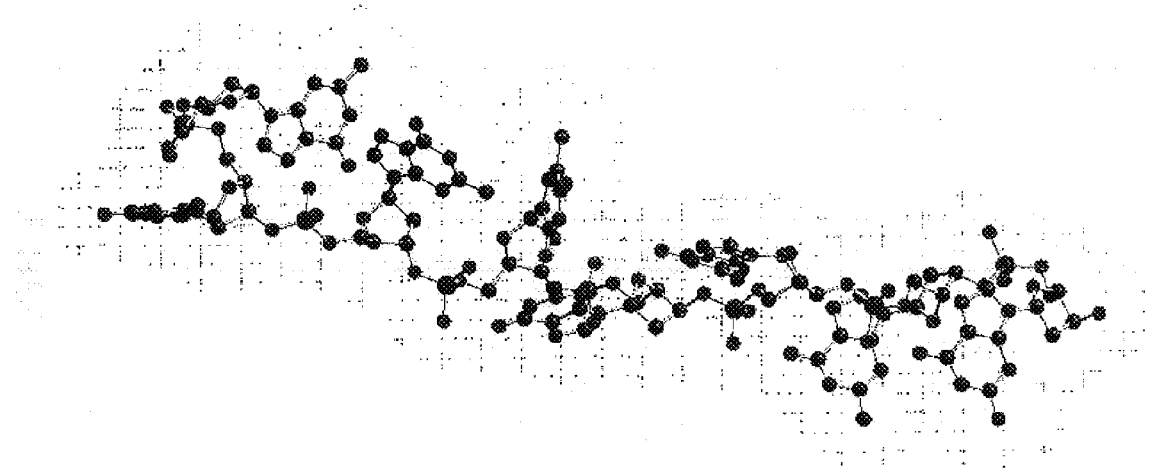
Figure 8C:
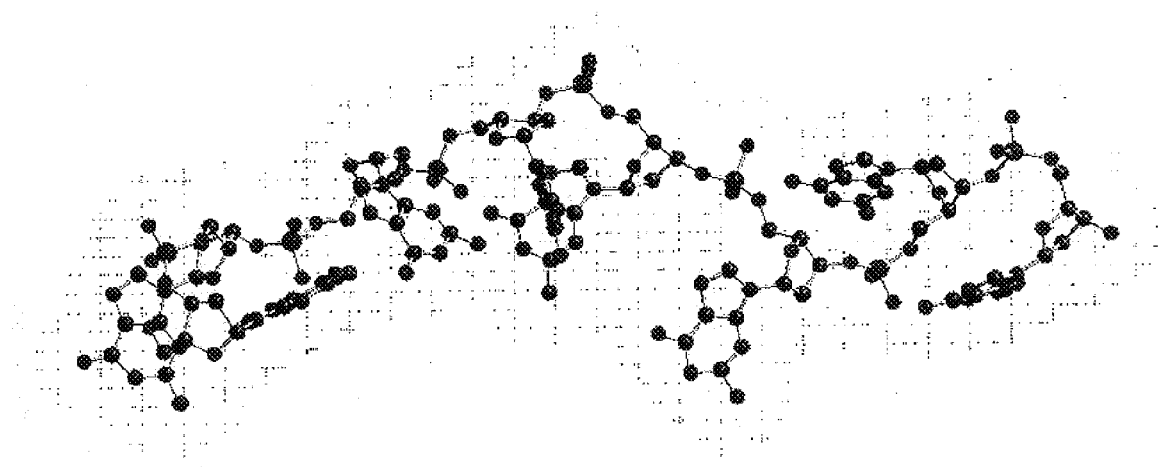
Figure 8D:
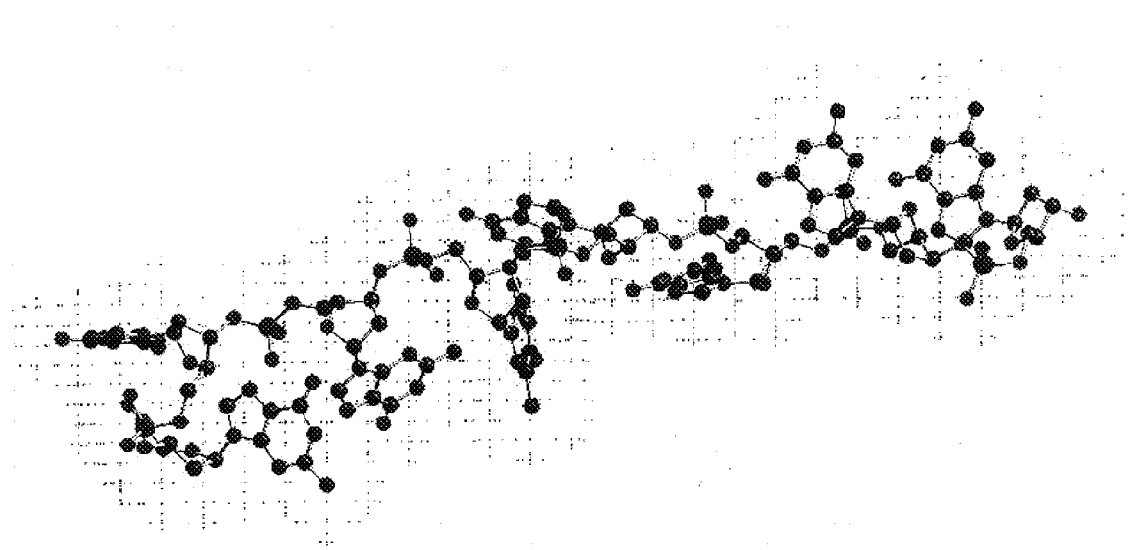
Figure 8E:
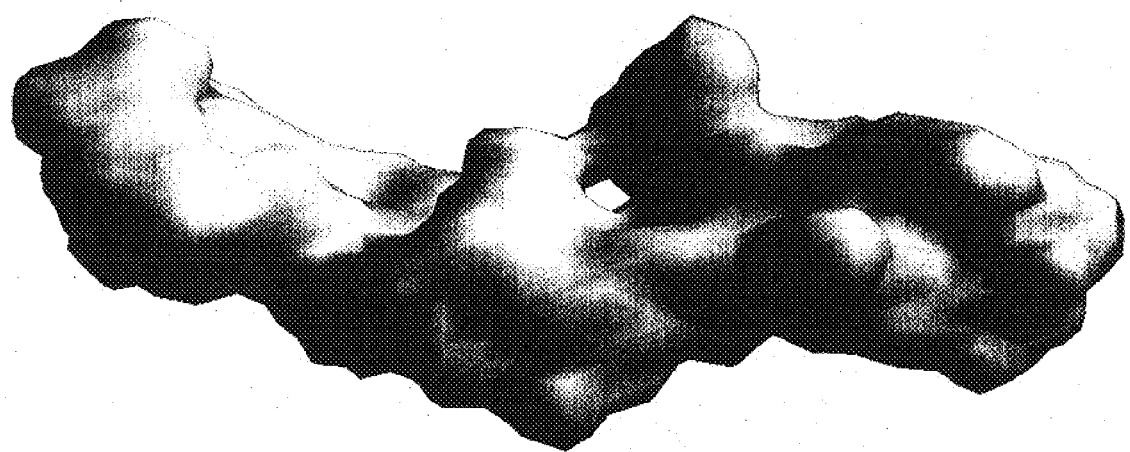
Figure 9A:
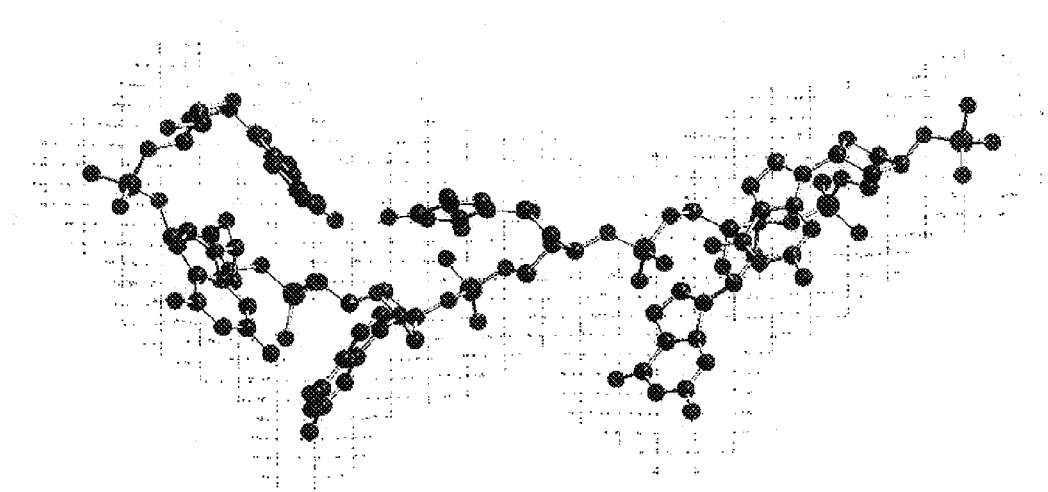
Figure 9B:
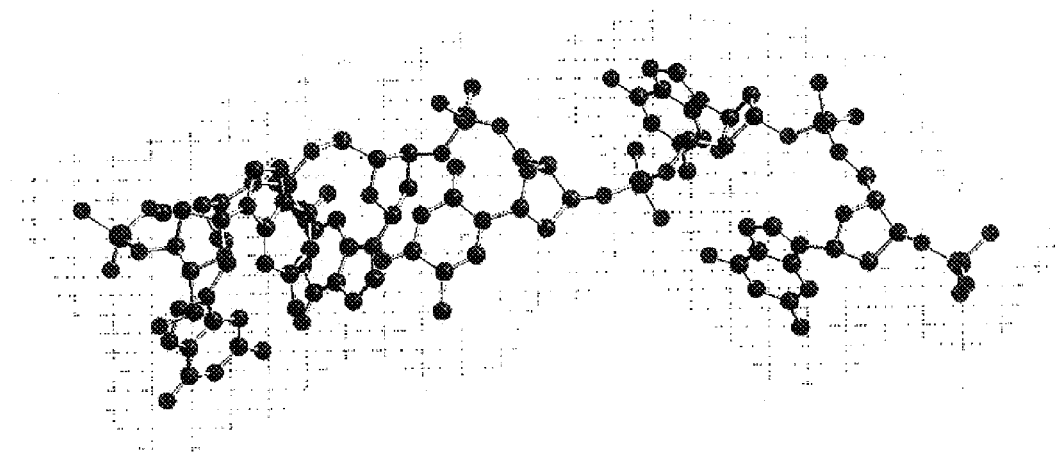
Figure 9C:
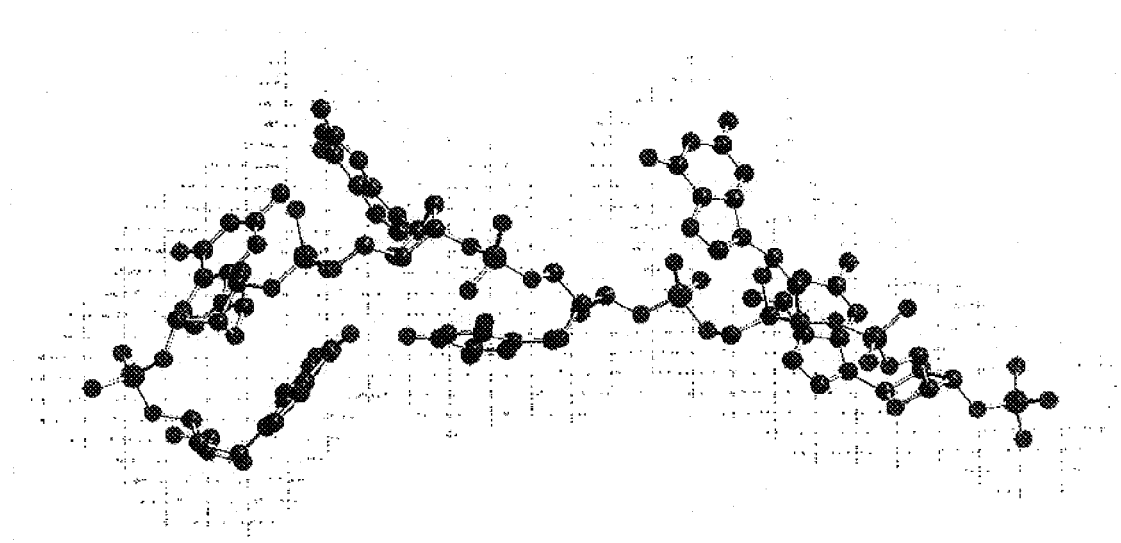
Figure 9D:
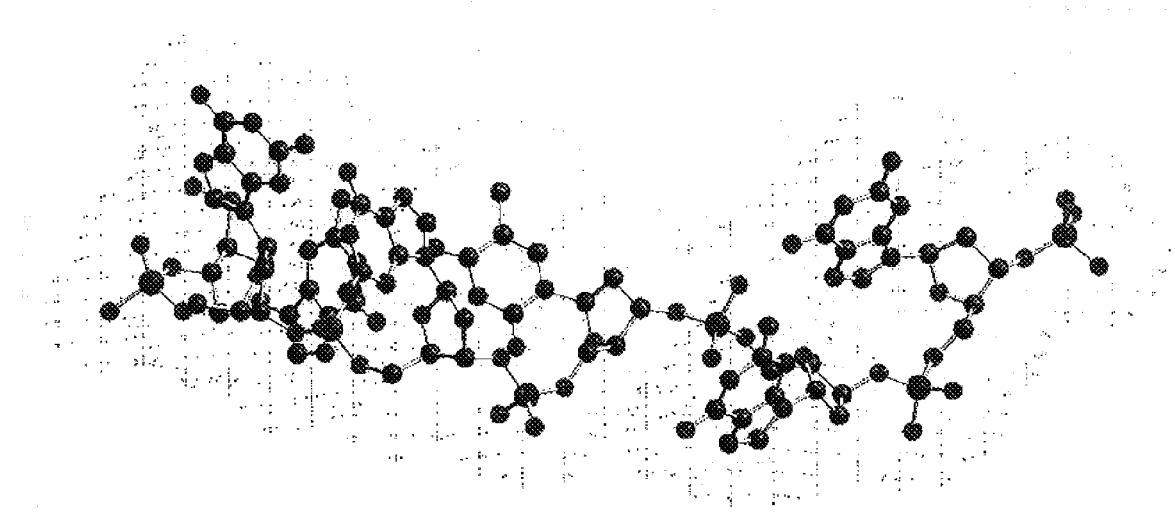
Figure 9E:
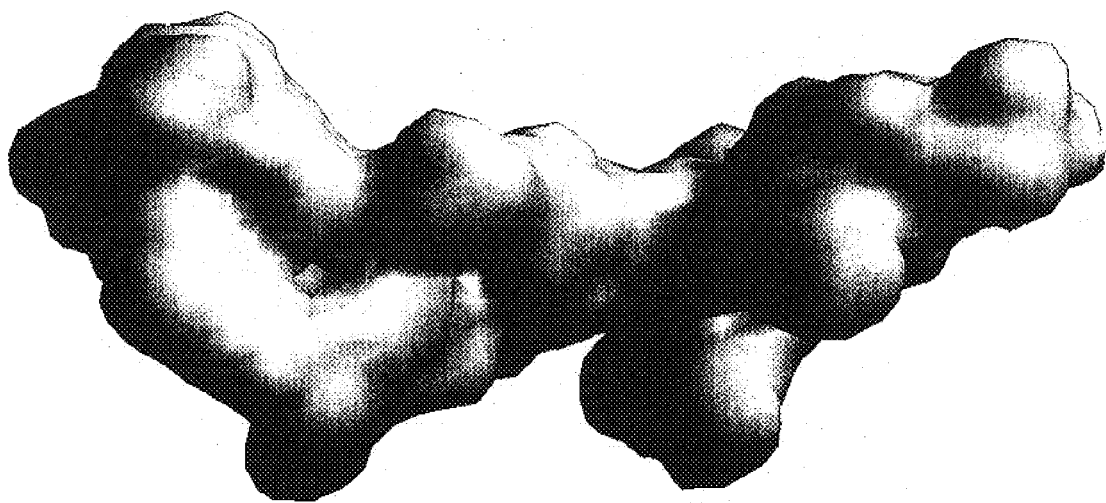
Figure 10A:
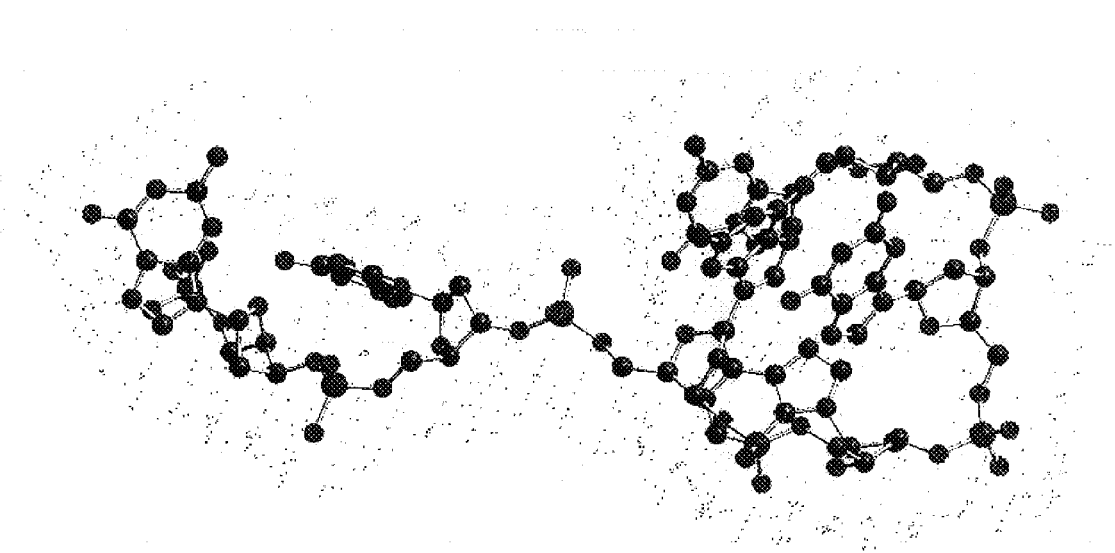
Figure 10B:
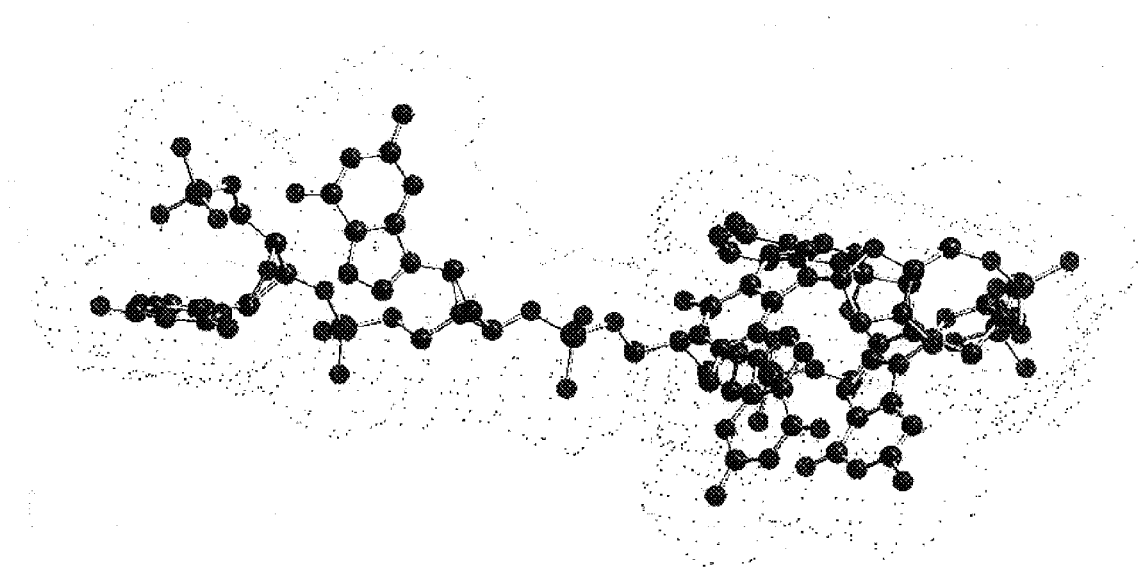
Figure 10C:
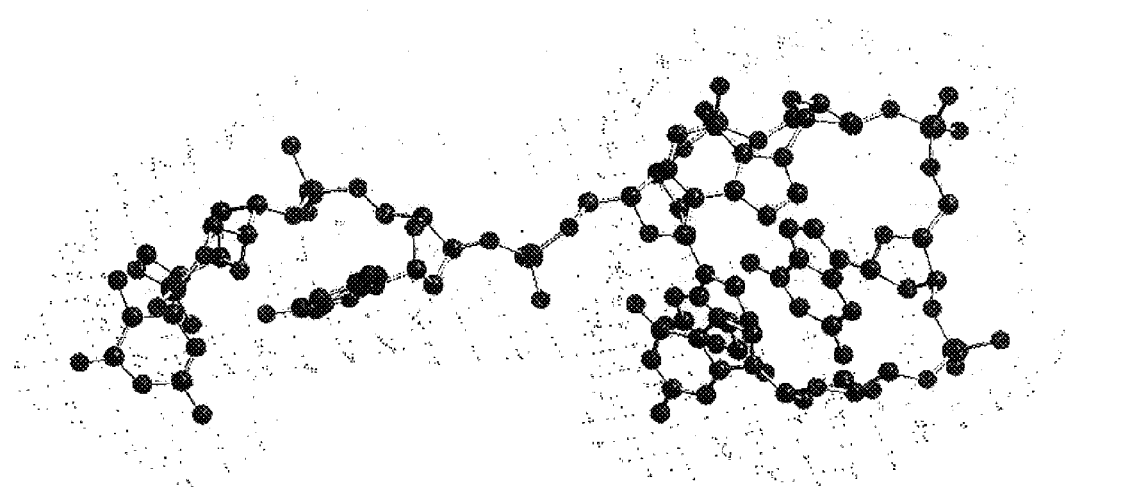
Figure 10D:
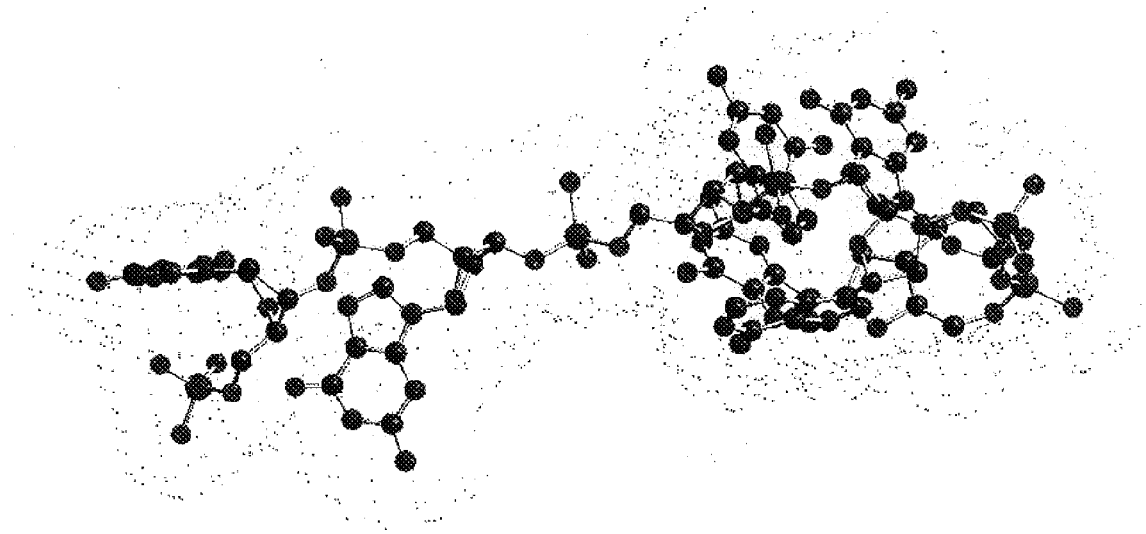
Figure 10E:
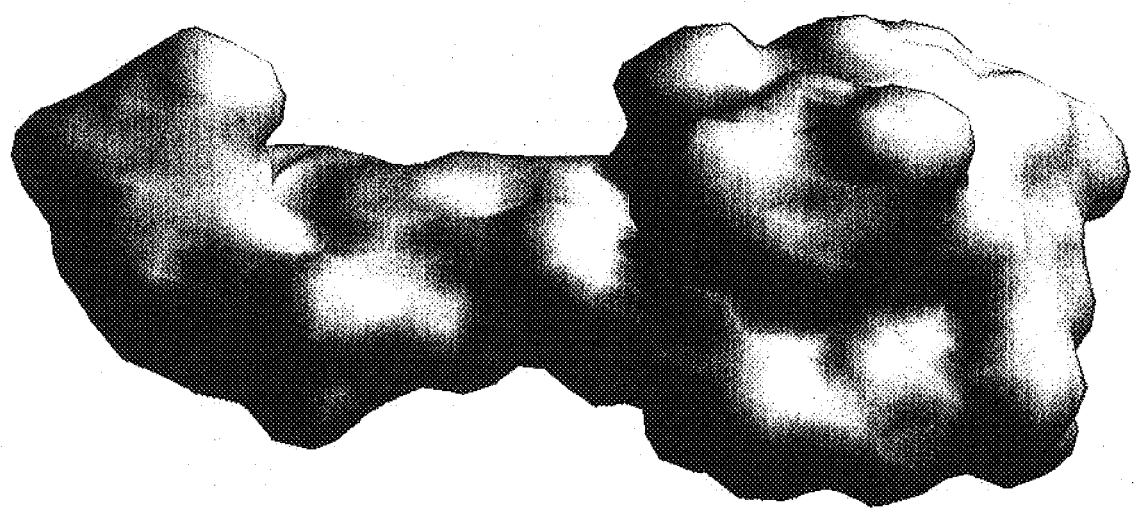
Figure 11A:
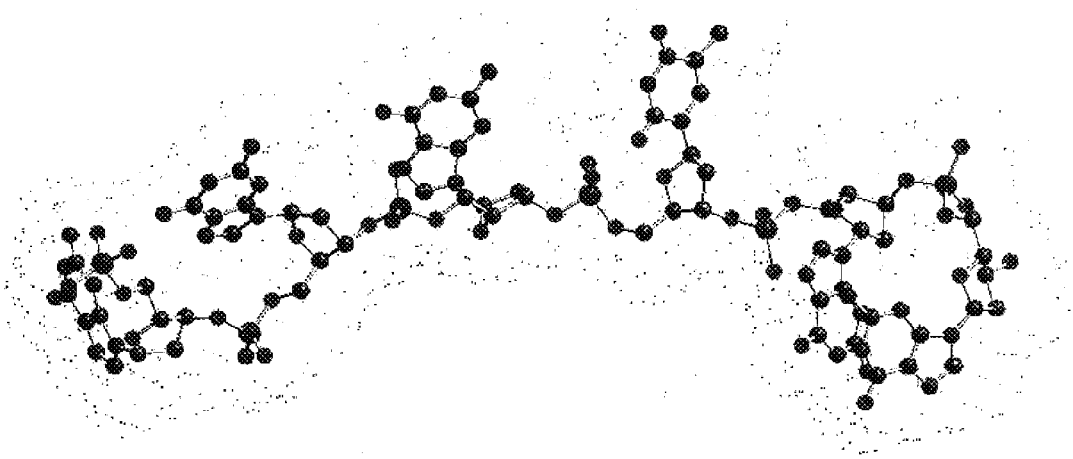
Figure 11B:
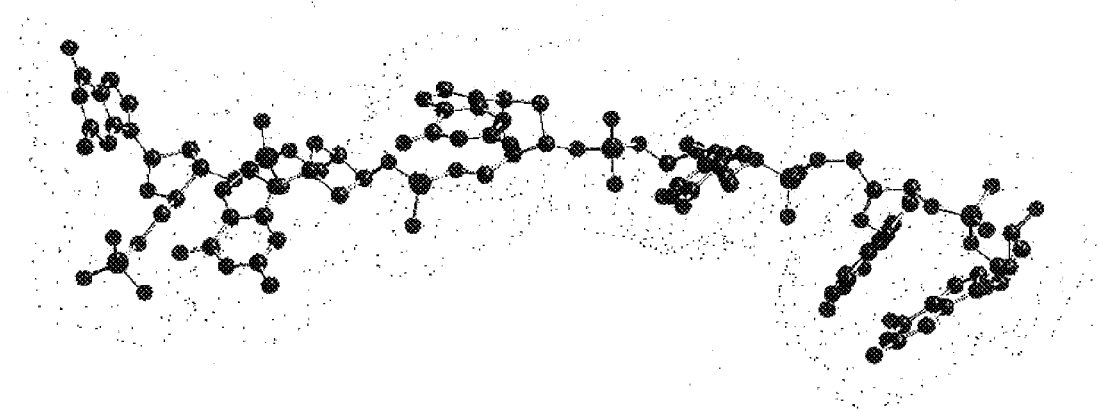
Figure 11C:
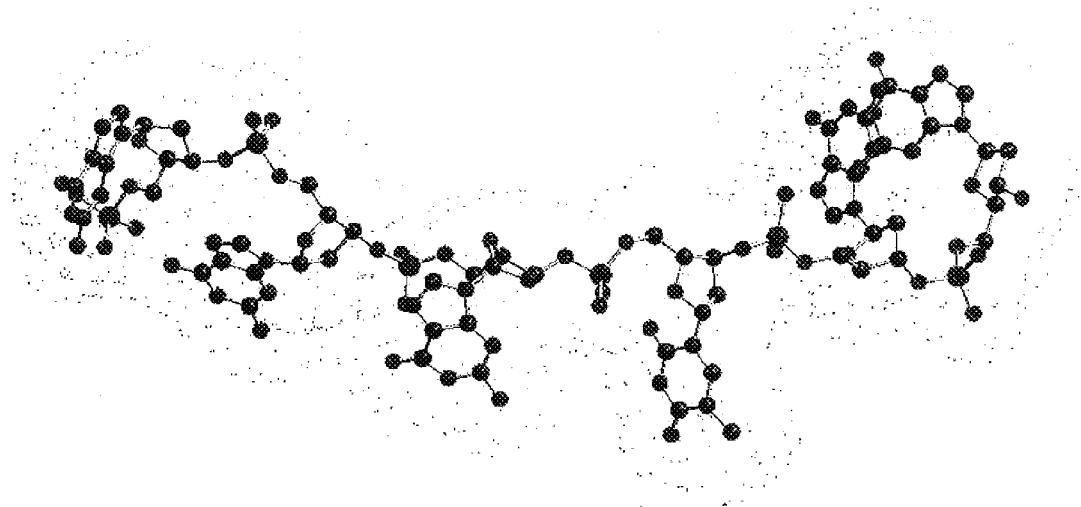
Figure 11D:
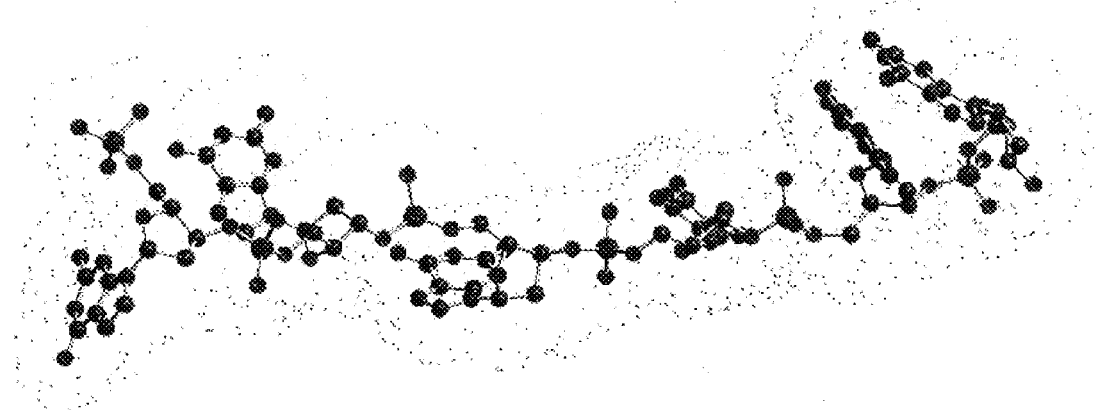
Figure 11E:
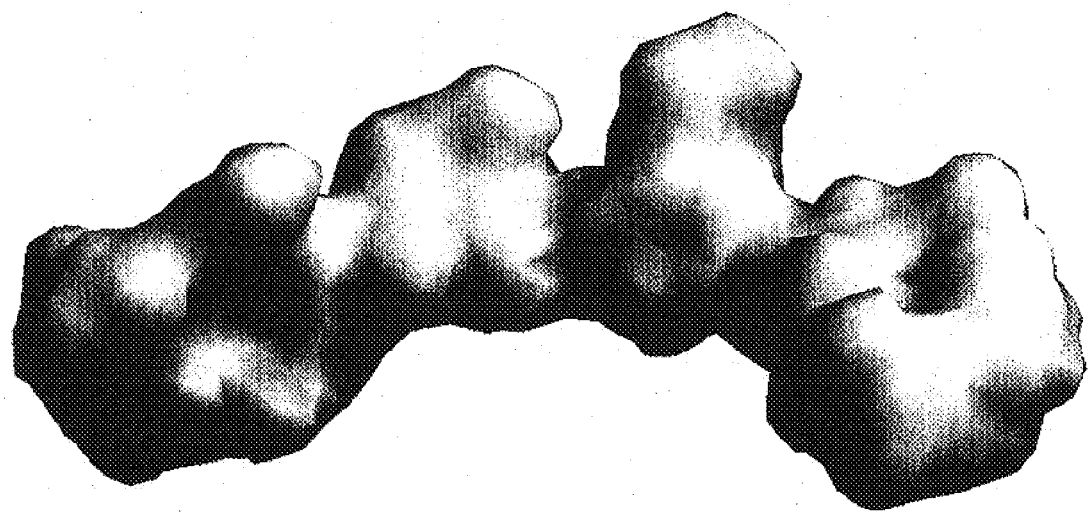
Figure 12A:
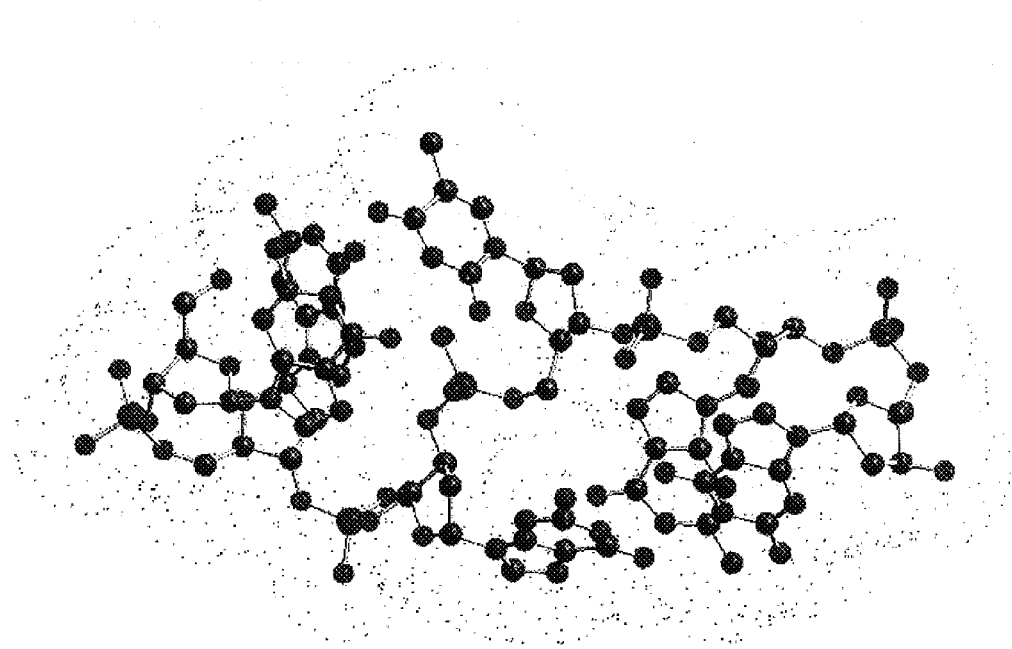
Figure 12B:
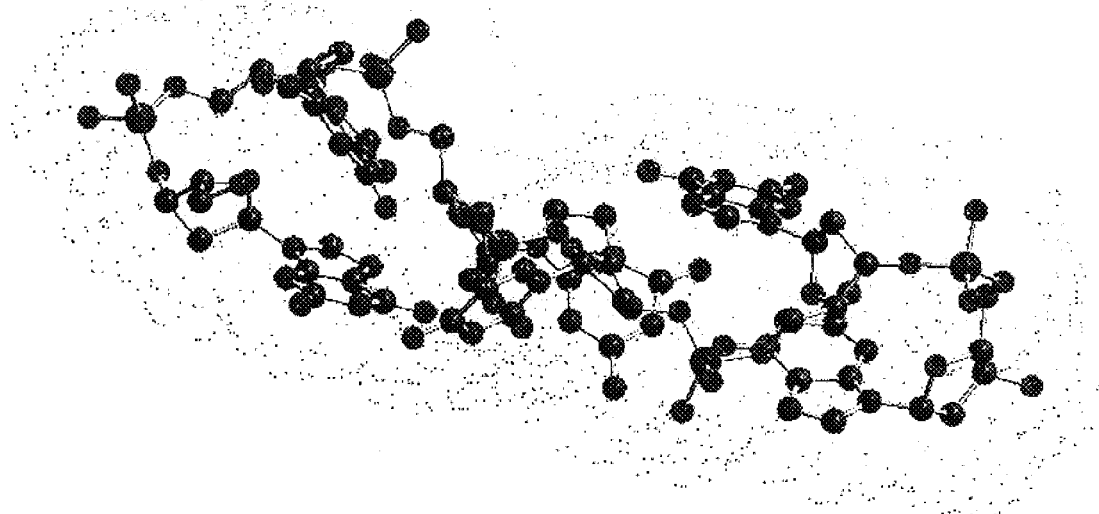
Figure 12C:
Figure 12D:
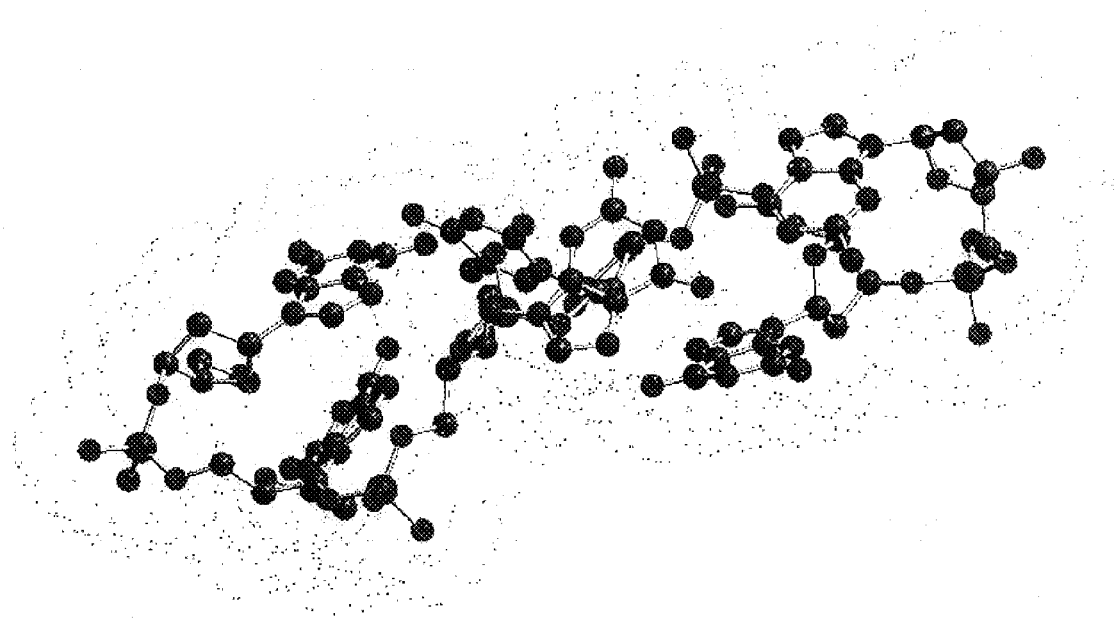
Figure 12E:
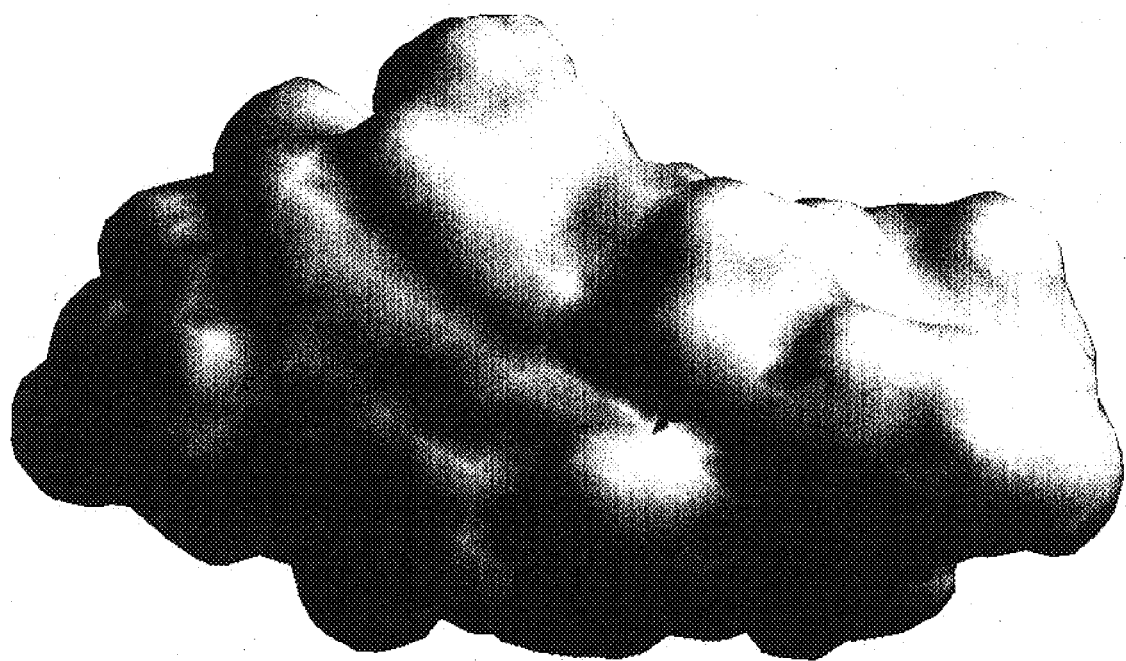
Figure 13A:
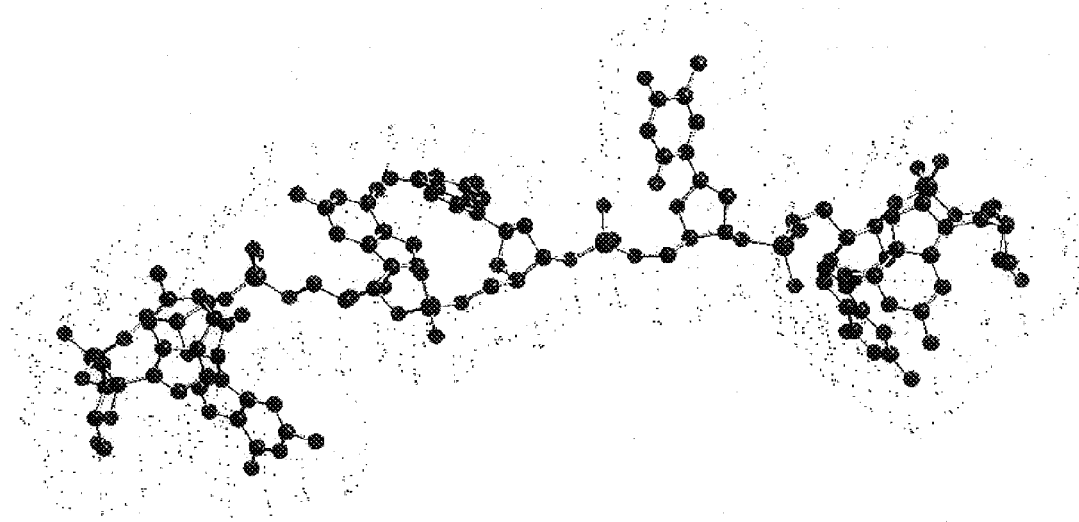
Figure 13B:
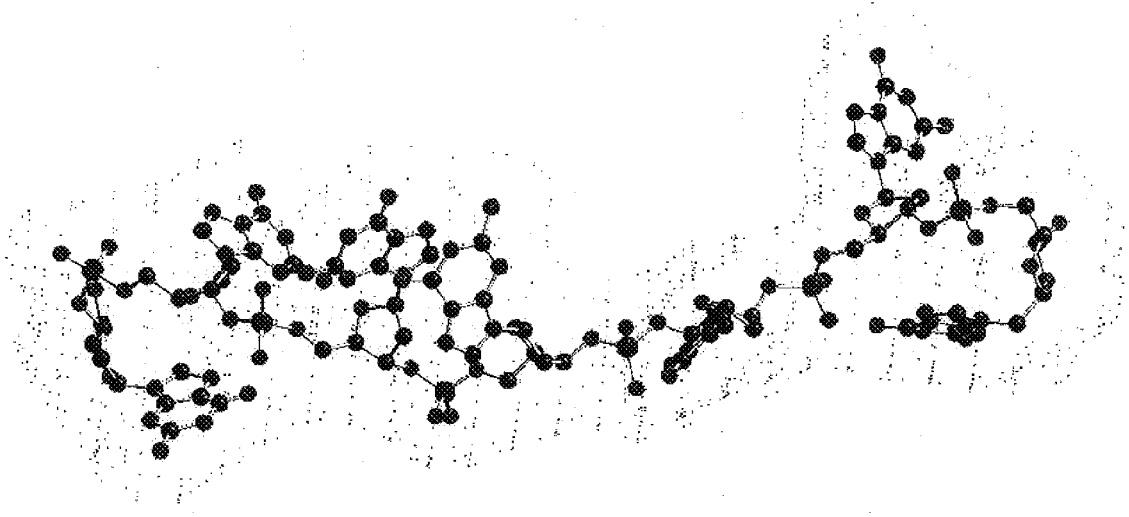
Figure 13C:
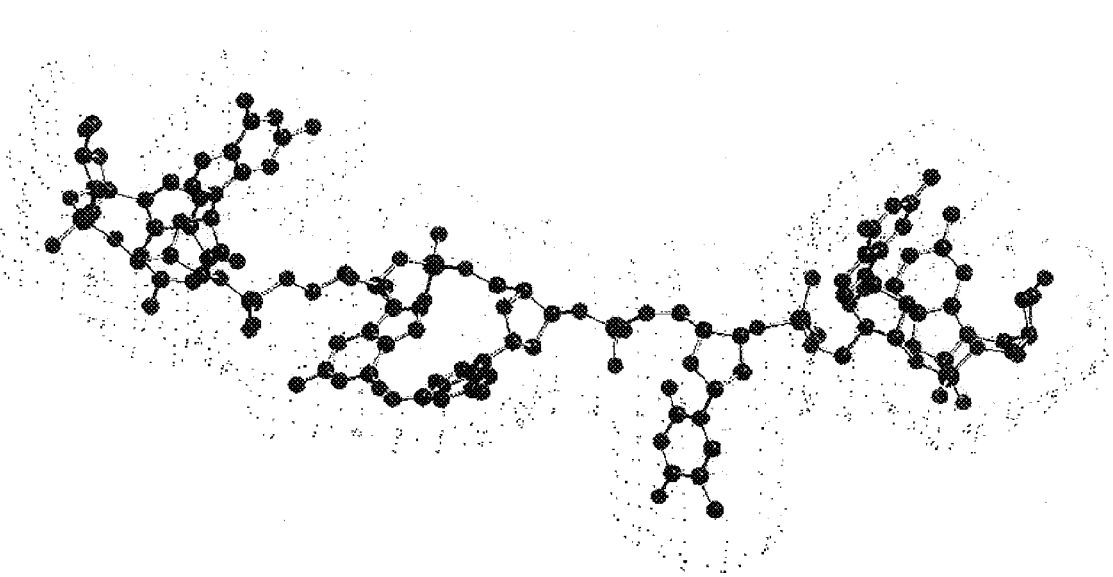
Figure 13D:
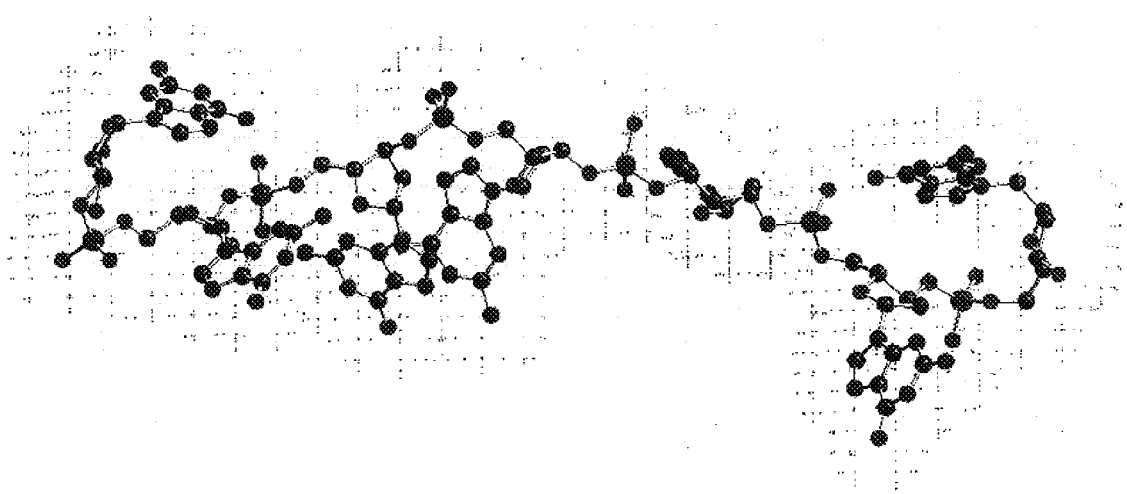
Figure 13E:
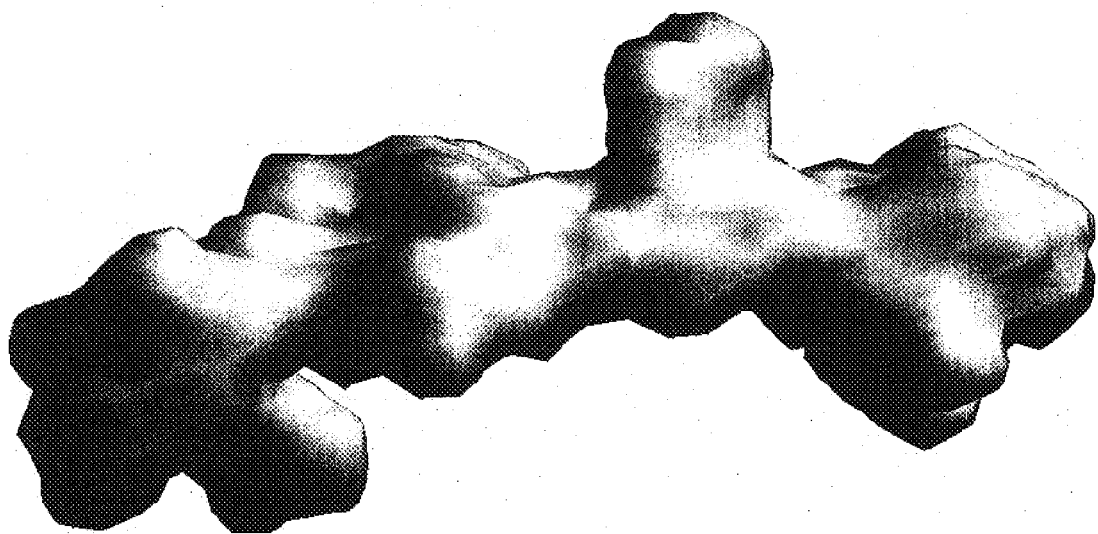

The following description of a centrum includes its key features. FIGS. 2a and 2b displays these features. FIG. 1 provides general orientation of a centrum (front, rear, ventral, dorsal, lateral left and lateral right).

Orientation of bases in the centrum. The centrum is defined as adjacent (type A) if bases are adjacent with a perpendicular orientation in the same or opposite plane to the phosphate necklace. The centrum is defined as non-adjacent (type B) if the order of the bases is not consecutive. A preferred orientation is type A or B, a more preferred orientation is type A and B, a most preferred orientation is type A with the bases in the same plane perpendicular to the phosphate necklace. one sequence can possess both type A and type B. If two centra were found in the given sequence then $A_1$ represents the first centrum at the 5' end and $A_2$ represents the second centrum at the 3' end.

Centrum phosphorus atoms. the x-axis represents the interatomic distance between phosphorus atoms associated with the centrum. If two phosphate atoms are involved (e.g. 5'-$N_{1p}N_{2p}N_3$-3' where $N_X$ represent purine or pyrimidine deoxyribonucleosides and P represents the phosphate group) then x is between approximately 700 to 1360 pm. If four phosphate atoms are involved then x is between approximately 750 to 1300 pm (e.g. 5'-$N_{1p}N_{2p}N_{3p}N_{4p}N_5$-3' where $N_x$ represent the number of purine or pyrimidine deoxyribonucleosides as an integer in the range 2 to 4, and P represents the number of phosphate groups as an integer).

Phosphate backbone-base distance. The Y-axis represents the longest distance between the phosphate backbone and the farthest atom of a participating base. This will depend on the rotation of the given base and which atom (group) is considered (methyl, carbonyl, or amino group). Y is equal to or between approximately 780 to 2200 pm. There is no preferred distance for Y.

Centrum depth. The Z-axis represents the distance from the front to the rear of the centrum when viewed from above. Z is equal to or between about 400 to 1300 pm. There is no preferred distance.

Amine/amido framing. The next defining parameter α is the furthest framing distance of the amino/amido group from the phosphate groups. The α distance is equal to or between about 900 and 1500 pm.

Amine/amido distance. The next defining parameter β is the furthest inter-atomic distance of amino/amido groups. The value is equal to or between about 300 to 1700 pm.

Intra-molecular hydrogen bonding. This bonding stabilizes the size and shape of molecules as well as the interatomic distances. Hydrogen bond distances should be equal to or less than about 300 pm. The most frequently observed bonding is via carbonyl groups and amino or amido groups. The next most frequent type of hydrogen bonding is between carbonyl groups and hydroxyl groups at the 3' or 5' end of the molecule. The last type of hydrogen bonding is between carbonyl groups and the hydroxyl groups of phosphates. A preferred type of hydrogen bonding comprises all three types, a more preferred hydrogen bonding is via carbonyl groups and amino/amido groups, and via carbonyl groups and phosphate groups, and a most preferred hydrogen bonding is via carbonyl and amino/amido groups.

Distance of the 5' or 3' end hydroxyls to their corresponding phosphate groups.

The last parameter is the distance of the 5' or 3' end hydroxyls to their corresponding phosphate groups. A preferred distance is equal to or between about 320 and 650 pm, a more preferred distance is equal to or between about 390 to 420 pm, and a most preferred distance is about 380 pm.

Randomly oriented molecules have bases that form fingers with necks separating individual fingers. These structures do not possess a centrum or centra as defined above and are either inactive or possess weak activity (<20% apoptosis-inducing activity, see Table 4).

The present invention demonstrates that a molecular combination of negative charges or electronegativity (for example from phosphate groups), positive charges or electropositivity (for example from amine and amido groups), in conjunction with appropriate intra-molecular hydrogen bonding and with X, Y, Z, α and β dimensions as defined above, possesses the ability to induce apoptosis in cancer cells. Accordingly the present invention provides a method of in silico analysis of molecular structures, particularly oligonucleotide structures, for prediction of apoptotic activity.

Three-dimensional computation is used to identify one or more 3-dimensional centrum or centra in oligonucleotide sequences or other molecules that comprise a molecular combination of negative charges or electronegativity (from phosphate groups), positive charges or electropositivity (from amine and amido groups), in conjunction with appropriate intra-molecular hydrogen bonding and with X, Y, Z, α and β dimensions as defined herein, and that on biological testing demonstrate the ability to induce apoptosis in cancer cells.

It is proposed that such a molecular combination of negative charges or electronegativity (from for example phosphate groups), positive charges or electropositivity (from for example amine and amido groups), in conjunction with appropriate intra-molecular hydrogen bonding and with X, Y, Z, α and β dimensions as defined above, will possess the ability to induce apoptosis in cancer cells. While such a molecular combination is described for oligonucleotide sequences, it is clear that this approach can be used to conduct molecular modeling and identification of apoptosis inducing centra in other molecular species.

In addition to the assay presented in Example 3 involving Annexin staining, other in vitro assays may optionally be employed to evaluate centrum-predicted biological activity of sequences. In vivo assays may also be employed. Various assays useful for this purpose are described in PCT CA00/01467, WO 01/44465, the entirety of which is incorporated herein by reference. Additional assays for evaluation of the efficacy of the sequences are described by Oncogene Research Products, P.O. Box 12087, La Jolla, Calif. 92039 (Apoptosis Catalog and Technical Guide 2002-2003, especially pages 5-295) the entirety of which is incorporated herein by reference. Such assays include assays designed to analyze DNA fragmentation, apoptosis, mitochondrial markers, endoplasmic reticulum markers, free nucleosomes, nuclear matrix proteins, detection and activity of numerous caspases and related proteins, including but not limited to caspases 1 through 14, glutathione, superoxide dismutase, members of the bcl-2 family, analysis of the Fas/TNR-R super family, PARP related products, analysis of apoptotic signal transducers, analysis of various signaling receptors including death receptors, Apo2, decoy receptors, analysis of apoptotic membrane proteins, nervous system apoptotic markers, numerous markers for cell cycle and cellular proliferation, mitotic kinases, bromodeoxyuridine assays, and p53 assays.. The evaluation of the efficacy of the sequences identified with the analytical method of the present invention may also be determined in the presence of other agents, and therapeutic agents, such as inducers of apoptosis and cell synchronization reagents as described by Oncogene Research Products, P.O. Box 12087, La Jolla, Calif., 92039 (Apoptosis Catalog and Technical Guide 2002-2003, especially pages 99-104 and pages 214-255, the entirety of which is incorporated herein by reference). Such agents include but are not limited to actinomycin D, amphidocolin, A23187, caffeine, camptothecin, cycloheximide, dexamethasone, doxorubicin, 5-fluorouracil, hydroxyurea, paclitaxel, staurosporine, thymidine, vinblastine, retinoic acid, etoposide, okadaic acid, vincristine and methotrexate.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Preparation of Deoxyribonucleic Acid Sequences

Phosphodiester and phosphorothioate sequences were prepared by Sigma-Genosys (Woodlands, Tex.) using Abacus Segmented Synthesis Technology. Unless stated otherwise, the sequences were dispersed in autoclaved deionized water or in a pharmaceutically acceptable buffer such as, but to limited to, saline immediately prior to use.

EXAMPLE 2

Cells and Treatment

Human Jurkat T cell leukemia cells were obtained from the American Type Culture Collection (Rockville, Md.). The Jurkat T cells were maintained RPMI 1640 medium, supplemented with 10% heat-inactivated (56° C., 30 min) fetal bovine serum (all from Sigma Aldrich, Canada) in an atmosphere of 5% $CO_2$ at 37° C. Cells were seeded at $2\times10^5$ cells/ml medium in 6-well float-bottomed tissue culture plates and incubated with oligonucleotides at a final concentration of 53 μM. Testing of other concentrations of the oligonucleotides demonstrated that they induced apoptosis in a concentration dependent manner.

EXAMPLE 3

Analysis of Apoptosis

Apoptosis was measured by staining cells with Annexin V FITC and propidium iodide (PI) (BD Pharmingen, San Diego, Calif. USA) according to the manufacturer's instructions. Flow Cytometry (FCM) determined cellular fluorescence. The FCM and data analysis were carried out using a FACSCalibur instrument (excitation 488 nm, emission 530 nm for Annexin-V and 580 nm for PI) using the program CELLQuest.

EXAMPLE 4

3 Dimensional Molecular Modeling

Chem3D version 5.0 and 6.0 software (CabridgeSoft Corporation, Cambridge, Mass.) was used to create 3-dimensional images of specific sequences. Molecular mechanics computation of minimal energy conformations (MM2; Allinger N. L., J. Comput. Chem., 1993, 14:755–68) was carried out at a default value 300° K using Newtonian mechanics to simulate motion of atoms, adding kinetic energy as the model's temperature increased. The values of molecular dynamics as well as the temperature range in which the molecular dynamics is valid are mentioned. 3-dimensional modeling was carried out in order to identify the absence or presence of intramolecular grouping, defined as a centrum. The spatial arrangement of electronegative charges (phosphate and base carbonyl groups, and electropositive charges (amino, amido, or hydroxyl groups at 3' and 5' ends) were also analyzed. When intramolecular grouping was observed in the 3-dimensional models, spatial characteristics were defined according to localization of phosphate groups, localization of amine/amido groups, and position of hydroxyl groups, or intramolecular grouping(s) in the oligonucleotides. The resulting structures are presented with the 5'-end at the left and 3'-end at the right.

The spatial orientation is characterized as shown in FIG. 1. Although not wanting to be bound by the following hypothesis, it is thought that the simplified ideal 3-dimensional sequence shown in FIG. 2a consists of phosphate groups (circles) and 2-deoxyribose units (cylinders) at the ventral position and horizontally oriented bases (prisms) at the dorsal side.

EXAMPLE 5

ODN with Relatively Weak (<20%) Apoptotic Activity

The results of the computational analysis and correlation with apoptosis-inducing activity are summarized in Table 1. Oligonucleotides containing between 3 and 8 bases and apoptosis values of less than 20% do not possess an identifiable 3-dimensional framed centrum. Typical illustrative 3-dimensional structures of sequences with weak apoptosis activity are shown in FIGS. 3, 4, and 5.

TABLE 1

Date of sequence with weak (<20%) apoptotic activity

| Number of bases | Sequence | Apoptosis (%) | Framed centrum | H bonds |
|---|---|---|---|---|
| 3 | TGT | 13 | 0 | No |
| 6 | CCGTCC | 5 | 0 | Yes |
|   | CTGTCT | 14 | 0 | Yes |
|   | GGGCGG | 17 | 0 | Yes |
|   | GGGGGG | 4 | 0 | No |
|   | TCGTTC | 9.5 | 0 | Yes |
|   | GGGTGG phosphorothioate | 0 | 0 | Yes |
| 7 | GGGGGTG | 11 | 0 | No |
| 8 | GGGGGTGG | 19 | 0 | Yes |

EXAMPLE 6

ODN with Intermediate (>20%<40%) Apoptotic Activity.

The results of the computational analysis and correlation with apoptosis-inducing activity are summarized in Table 2. Oligonucleotides containing between 3 and 8 bases and apoptosis activity of >20%<40% possessed an identifiable centrum of either type A or type B. Typical illustrative 3-dimensional structures are shown in FIGS. 6–8.

TABLE 2

Data of sequences with intermediate apoptotic activity

| # of bases | Sequence | % apoptosis | Framed centrum | Centrum type | P number/ number of bases | X(pm) | Y(pm) | Z(pm) | Alpha (pm) | Beta (pm) | H bond |
|---|---|---|---|---|---|---|---|---|---|---|---|
| 3 | GTG | 27 | 1 | A | 3/2 | 721 | 1252 | 759 | 1150 | 994 | Yes |
| 4 | GTGG | 23 | 1 | A | 4/3 | 1262 | 1219 | 863 | 1125 | 936 | Yes |
| 5 | GGTGG | 21 | 1 | A | 3/4 | 1202 | 1403 | 882 | 1207 | 757 | Yes |
| 6 | AAGTAA | 23 | 1 | A | 2/2 | 728 | 1064 | 672 | 916 | 751 | No |
|   | ATGTAT | 37 | 1 | A | 2/2 | 748 | 998 | 599 | 934 | 428 | Yes |
|   | GGCCGG | 21 | 1 | B | 2/4 | 776 | 1093 | 882 | 1414 | 731 | Yes |
|   | TTGTGG | 38 | 1 | A | 2/2 | 737 | 783 | 553 | 970 | 726 | Yes |
|   | GGGTGGG | 29 | 1 | A | 3/3 | 702 | 1149 | 893 | 982 | 853 | Yes |
| 8 | GGGTGGGG | 23 | 1 | A | 2/2 | 777 | 1342 | 848 | 948 | 1157 | Yes |

EXAMPLE 7

ODN with High (≧41%≦80% Apoptosis) Activity

The results of the computational analysis and correlation with apoptosis-inducing activity are summarized in Table 3. Oligonucleotides containing between 3 and 7 bases and apoptosis activity of ≧41%≦80% possessed an identifiable centrum of either type A or type B. Typical illustrative 3-dimensional structures are shown in FIGS. 9–13.

EXAMPLE 8

Influence of Phosphodiester Versus Phosphorothioate Backbone On 3-Dimensional Conformation and Apoptotic Activity Comparison of the activity and 3-dimensional conformation of sequence GGGTGG with a phosphodiester backbone (Table 3 and FIG. 12) and GGGTGG with a phosphorothioate backbone (Table 1 and FIG. 5) shows that the change in apoptosis-inducing activity (50% and 0% respectively) correlates with a loss of a framed centrum of strong electronegativity due to the prevailing planar orientation of the first three Gs, as well as the amino group of $G_4$ at the frontal bottom and the one of $G_5$ at the dorsal top excludes the last two Gs from the framed centrum.

TABLE 3

Data of sequences with high apoptotic activity

| # of bases | Sequence | % apoptosis | Framed centrum | Centrum type | P number/ number of bases | X(pm) | Y(pm) | Z(pm) | Alpha (pm) | beta(pm) | H bond |
|---|---|---|---|---|---|---|---|---|---|---|---|
| 4 | GGTG | 42 | 1 | B | 3/3 | 1123 | 1393 | 898 | 1118 | 1257 | Yes |
| 5 | GGGTG | 46 | 1 | A | 2/2 | 724 | 1159 | 652 | 1049 | 818 | Yes |
|   | GTGGG | 46 | 1 | A | 2/3 | 658 | 1152 | 411 | 1180 | 826 | Yes |
| 6 | GGGTGG__3P | 46 | 1 | A | 3/3 | 1423 | 3132 | 1566 | 1174 | 967 | Yes |
|   | 5P_GGGTGG | 62 | 2 | $A_1$ | 3/3 | 1250 | 1125 | 845 | 1719 | 1793 | Yes |
|   | 5P_GGGTGG |   |   | $A_2$ | 2/2 | 747 | 1085 | 514 | 821 | 609 | Yes |
|   | GGAAGG | 59 | 1 | B | 3/4 | 901 | 1262 | 759 | 1451 | 1396 | Yes |
|   | GGTTGG | 66 | 1 | A | 2/2 | 748 | 947 | 698 | 881 | 306 | Yes |
|   | GGGTGG | 50 | 1 | A | 2/2 | 753 | 1149 | 674 | 1101 | 613 | Yes |
|   | GTGGTG | 43 | 1 | A | 3/4 | 1440 | 2197 | 1288 | 1191 | 1333 | Yes |
|   | GTGTGT | 67 | 1 | A | 3/3 | 1038 | 1686 | 1232 | 1222 | 1471 | Yes |
|   | TGGTTG | 69 | 2 | $A_1$ | 2/2 | 788 | 1054 | 949 | 1007 | 631 | Yes |
|   | TGGTTG |   |   | $A_2$ | 2/2 | 725 | 881 | 725 | 937 | 514 | Yes |
|   | TGTGTG | 66 | 1 | A | 3/3 | 887 | 1527 | 1231 | 1522 | 1086 | Yes |
| 7 | GGGGTGG | 44 | 1 | A | 2/2 | 702 | 1149 | 893 | 982 | 853 | Yes |

EXAMPLE 9

3' or 5' Modification Does Not Result in the Loss of Apoptosis-Inducing Centra

3' modified sequences GGGTGG-phosphate (Table 3, FIG. 9), 5'-modified sequence phosphate-GGGTGG (Table 3, FIG. 11) all contained a framed centrum. 3', 5' or 3', 5'-modification of oligonucleotides containing a centrum of activity does not result in conformational changes that lead to the loss of such centra.

EXAMPLE 10

Prediction of the Apoptotic Efficacy of a Sequence

The sequences in Table 4 were analyzed with the method of the present invention to determine if they possessed a centrum. A prediction was made as to whether the sequences would possess the ability to induce apoptosis, arbitrarily set at 20%. In other words, a prediction of apoptotic activity implied activity greater than 20%. Subsequently, the sequences were tested in vitro for apoptotic activity. The results are shown in Table 4 and indicate a very high success rate in predicting apoptotic activity. The method was successful for each sequence analyzed. These data demonstrate that the in silico method of the present invention identifies sequences with different degrees of apoptotic activity, thereby providing a basis for prioritizing selection of sequences for biological testing.

TABLE 4

Predictive value of the method using new sequences with unknown apoptosis-inducing activity

| SEQUENCE | PRESENCE OF A CENTRUM YES | PRESENCE OF A CENTRUM NO | PREDICTED APOPTOTIC ACTIVITY No | PREDICTED APOPTOTIC ACTIVITY Yes | ACTUAL % OF CELLS IN APOPTOSIS |
|---|---|---|---|---|---|
| GCG-(3 bases) | X |   |   | X | 25 |
| GGAG-(4 bases) | X |   |   | X | 35 |

TABLE 4-continued

Predictive value of the method using new sequences with unknown apoptosis-inducing activity

| SEQUENCE | PRESENCE OF A CENTRUM YES | PRESENCE OF A CENTRUM NO | PREDICTED APOPTOTIC ACTIVITY No | PREDICTED APOPTOTIC ACTIVITY Yes | ACTUAL % OF CELLS IN APOPTOSIS |
|---|---|---|---|---|---|
| AGTA-(4 bases) |   | X | X |   | 12 |
| GAGG-(4 bases) |   | X | X |   | 17 |
| GGAG-(4 bases) | X |   |   | X | 35 |
| GAGGG-(5 bases) | X |   |   | X | 66 |
| GGGAG-(5 bases) | X |   |   | X | 73 |
| GGGGAG-(6 bases) | X |   |   | X | 33 |
| GAGGGG-(6 bases) |   | X | X |   | 13 |
| GAGGGGG-(7 bases) |   | X | X |   | 5 |
| GGGAGGGG-(8 bases) | X |   |   | X | 76 |
| GGGGGAGG-(8 bases) |   | X | X |   | 11 |
| AAAGTAAA-(8 bases) |   | X | X |   | 6 |

It is to be understood that the foregoing relates only to a preferred embodiment of the present invention and that numerous modifications or alterations may be made therein without departing from the spirit and scope of the invention as set forth in the appended claims.

We claim:

1. A computer-based method of predicting biological activity of an oligonucleotide sequence comprising:
   drawing the oligonucleotide sequence using chemical drawing software;
   creating a three dimensional model of the drawn sequence;
   displaying a solvent accessible surface of the three dimensional model on a display means;
   identifying globular and linear domains in the three dimensional model;
   identifying phosphates in a globular domain which form a phosphate necklace;
   evaluating spatial orientation of bases in the three dimensional model for electropositive framing with respect to the phosphates in the globular domain;

measuring a first interatomic distance X between a first phosphate and a last phosphate of the globular domain;

measuring a second interatomic distance alpha between the first phosphate of the globular domain and an amido/amino group in the base attached to the first phosphate of the globular domain;

measuring a third interatomic distance beta as the furthest interatomic distance between amido or amino groups in the globular domain;

measuring a fourth interatomic distance Z as a distance between one side of the oligonucleotide sequence and an opposite side of the oligonucleotide sequence; and, measuring a fifth interatomic distance Y as a longest distance between the first phosphate of the globular domain and the farthest atom in the base attached to the first phosphate of the globular domain; and, predicting that the oligonucleotide sequence has biological activity if the oligonucleotide sequence contains at least one centrum.

2. The method of claim 1, wherein a centrum is present in the sequence if Y is equal to or between about 780 to 2200 pm; Z is equal to or between about 400 to 1300 pm; alpha is equal to or between about 900 and 1500 pm; beta is equal to or between about 300 to 1700 pm; and, X is approximately 700 to 1360 pm.

3. The method of claim 1, wherein the method further comprises:
checking the drawn sequence for errors;
minimizing energy of the three dimensional model;
calculating molecular dynamics using chemical analytical software; and,
identifying intramolecular hydrogen bonds.

4. The method of claim 1, wherein the biological activity is inhibition of cellular proliferation, induction of cell cycle arrest or induction of apoptosis.

5. The method of claim 1, further comprising testing the sequence for the biological activity.

6. A computer-based method of predicting biological activity of an oligonucleotide sequence comprising:
drawing the oligonucleotide sequence using chemical drawing software;
creating a three dimensional model of the drawn sequence;
displaying a solvent accessible surface of the three dimensional model on a display means;
identifying globular and linear domains in the three dimensional model;
identifying phosphates in a globular domain which form a phosphate necklace
evaluating spatial orientation of bases in the three dimensional model for electropositive framing with respect to the phosthates in the globular domain;
measuring a first interatomic distance X between a first phosphate and a last phosphate of the globular domain;
measuring a second interatomic distance alpha between the first phosphate of the globular domain and an amido/amino group in the base attached to the first phosphate of the gobular domain;
measuring a third interatomic distance beta as the furthest interatomic distance beta between amido or amino groups in the globular domain;
measuring a fourth interatomic distance Z as a distance between one side of the oligonucleotide sequence and an opposite side of the oligonucleotide sequence; and, measuring a fifth interatomic distance Y as a longest distance between the first phosphate of the globular domain and the farthest atom in the base attached to the first phosphate of the globular domain;

wherein a centrum is present the oligoriucleotide sequence if Y is equal to or between about 780 to 2200 pm; Z is equal to or between about 400 to 1300 pm; alpha is equal to or between about 900 and 1500 pm; beta is equal to or between about 300 to 1700 pm; and, X is approximately 700 to 1360 pm; and, predicting that the oligonucleotide sequence has biological activity if the oligonucleotide sequence contains at least one centrum.

7. The method of claim 6, wherein the biological activity is inhibition of cellular proliferation, induction of cell cycle arrest or induction of apoptosis.

8. The method of claim 6, further comprising testing the sequence for the biological activity.

9. The method of claim 6, wherein the method further comprises;
checking the drawn sequence for errors;
minimizing energy of the three dimensional model;
calculating molecular dynamics using chemical analytical software; and,
identifying intramolecular hydrogen bonds.

10. A method for analyzing an oligonucleotide sequence to determine if the oligonucleotide sequence possesses a centrum, comprising:
drawing the oligonueleotide sequence using chemical drawing software;
creating a three dimensional model of the drawn sequence;
displaying a solvent accessible surface of the three dimensional model on a display means;
identifying globular and linear domains in the three dimensional model;
identifying phosphates in a globular domain which form a phosphate necklace;
evaluating spatial orientation of bases in the three dimensional model for electropositive framing with respect to the phosphates in the globular domain;
wherein a centrum is present in the oligonucleotide sequence if Y is equal to or between about 780 to 2200 pm; Z is equal to or between about 400 to 1300 pm; alpha is equal to or between about 900 and 1500 pm; beta is equal to or between about 300 to 1700 pm; and, X is approximately 700 to 1360 pm.

11. A computer-based method of predicting biological activity of an oligonucleotide sequence comprising:
drawing the oligonucleotide sequence using chemical drawing software;
creating a three dimensional model of the drawn sequence;
identifying globular and linear domains in the three dimensional model;
identifying phosphates in a globular domain which form a phosphate necklace;
evaluating spatial orientation of bases in the three dimensional model for electropositive framing with respect to the phosphates in the globular domain;
wherein a centrum is present in the oligonucleotide sequence if Y is equal to or between about 780 to 2200 pm; Z is equal to or between about 400 to 1300 pm; alpha is equal to or between about 900 and 1500 pm; beta is equal to or between about 300 to 1700 pm; and, X is approximately 700 to 1360 pm; and, predicting that the oligonucleotide sequence has biological activity if the oligonucleotide sequence contains the centrum.

12. The computer-based method of claim 11 wherein X is the distance between a first phosphate and a last phosphate in the globular domain;

alpha is the distance between the first phosphate and the amido/amido group in a base attached to the first phosphate of the globular domain;

beta is the furthest interatomic distance between amido or amino groups in the globular domain;

Z is the distance between one side of the oligonucleotide sequence and an opposite side of the oligonucleotide sequence; and, Y is the longest distance between the first phosphate of the globular domain and the farthest atom a base attached to the first phosphate of in the globular domain.

13. The method of claim 11, wherein the biological activity is inhibition of cellular proliferation, induction of cell cycle arrest or induction of apoptosis.

14. The method of claim 11, further comprising testing the sequence for the biological activity.

15. The method of claim 11, wherein the centrum is type A.

16. The method of claim 11, wherein the centrum is type B.

* * * * *